(12) United States Patent
Kurono

(10) Patent No.: US 11,604,201 B2
(45) Date of Patent: Mar. 14, 2023

(54) SPECIMEN ANALYZER AND SPECIMEN ANALYSIS METHOD

(71) Applicant: SYSMEX CORPORATION, Kobe (JP)

(72) Inventor: Hiroshi Kurono, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 528 days.

(21) Appl. No.: 16/697,423

(22) Filed: Nov. 27, 2019

(65) Prior Publication Data
US 2020/0174028 A1 Jun. 4, 2020

(30) Foreign Application Priority Data
Nov. 30, 2018 (JP) .............................. JP2018-225370

(51) Int. Cl.
*G01N 35/00* (2006.01)
*G01D 3/00* (2006.01)
*G01N 33/49* (2006.01)

(52) U.S. Cl.
CPC ......... *G01N 35/00594* (2013.01); *G01D 3/00* (2013.01); *G01N 33/4905* (2013.01);
(Continued)

(58) Field of Classification Search
CPC ......... G01N 35/00594; G01N 33/4905; G01N 35/00871; G01N 2035/00633;
(Continued)

(56) References Cited

U.S. PATENT DOCUMENTS

| 6,579,717 B1 | 6/2003 | Matsubara et al. |
| 2005/0037502 A1 | 2/2005 | Miller |

(Continued)

FOREIGN PATENT DOCUMENTS

| CN | 105807072 A | 7/2016 |
| EP | 3037825 A1 | 6/2016 |

(Continued)

OTHER PUBLICATIONS

Extended European search report dated Apr. 22, 2020 in a counterpart European application No. 19212135.8.
(Continued)

*Primary Examiner* — Jill A Warden
*Assistant Examiner* — John McGuirk
(74) *Attorney, Agent, or Firm* — Crowell & Moring LLP

(57) ABSTRACT

Disclosed is a specimen analyzer configured to perform analysis on a specimen for a plurality of measurement items, the specimen analyzer including a measurement section configured to perform a specimen measurement for measuring a measurement sample prepared from a specimen and a reagent corresponding to a measurement item, and configured to perform a quality control measurement for measuring a measurement sample prepared from a quality control substance and a reagent corresponding to a measurement item; and a controller programmed to set a quality control for each measurement item, from a quality control group that includes at least two types of quality controls selected from a first quality control in which the quality control measurement is performed at a predetermined time, a second quality control in which the quality control measurement is performed every time the specimen measurement is performed a predetermined number of times of measurement, and a third quality control in which the quality control measurement is performed every predetermined time interval, the
(Continued)

| MEASUREMENT ITEM | TIME QC | TIME | TIME INTERVAL QC | TIME INTERVAL | TEST NUMBER QC | TEST NUMBER | VIAL QC |
|---|---|---|---|---|---|---|---|
| APTT-FSL | ON | 9:00 | OFF | 8 | OFF | 120 | ON |
| APL | ON | 10:00 | OFF | 6 | OFF | 150 | OFF |
| AT3 | OFF | 9:00 | ON | 8 | OFF | 200 | ON |
| Plg | OFF | 10:00 | OFF | 8 | ON | 190 | ON |
| PC | OFF | 10:00 | ON | 7 | OFF | 160 | OFF |
| DD wide | OFF | 9:00 | OFF | 6 | ON | 250 | OFF |
| XIII ch | OFF | 10:00 | ON | 5 | OFF | 230 | OFF |
| VII | ON | 9:00 | OFF | 8 | OFF | 210 | ON |
| VIII-FSL | OFF | 9:00 | OFF | 7 | ON | 150 | OFF |
| Fbg | OFF | 10:00 | OFF | 8 | ON | 110 | OFF | controller being programmed to control the measurement section in accordance with the set quality control.

19 Claims, 25 Drawing Sheets

(52) U.S. Cl.
CPC ............... *G01N 35/00871* (2013.01); *G01N 2035/00633* (2013.01); *G01N 2035/00673* (2013.01)

(58) Field of Classification Search
CPC ... G01N 2035/00673; G01N 35/00712; G01N 35/00663; G01D 3/00
See application file for complete search history.

(56) References Cited

U.S. PATENT DOCUMENTS

| | | |
|---|---|---|
| 2008/0219887 A1 | 9/2008 | Akutsu |
| 2010/0210019 A1 | 8/2010 | Kurono et al. |
| 2011/0200485 A1 | 8/2011 | Akutsu |
| 2013/0011298 A1 | 1/2013 | Itou et al. |
| 2013/0039809 A1 | 2/2013 | Akutsu |
| 2015/0269513 A1 | 9/2015 | Kaneko et al. |
| 2016/0161521 A1* | 6/2016 | Sakairi .............. G01N 35/025 422/67 |

FOREIGN PATENT DOCUMENTS

| | | | |
|---|---|---|---|
| JP | H3-255366 | A | 11/1991 |
| JP | H0465676 | A | 3/1992 |
| JP | H10-2902 | A | 1/1998 |
| JP | H10-339732 | A | 12/1998 |
| JP | H11-108934 | A | 4/1999 |
| JP | 2003-240698 | A | 8/2003 |
| JP | 2004-156971 | A | 6/2004 |
| JP | 2004271265 | A | 9/2004 |
| JP | 2006-53164 | A | 2/2006 |
| JP | 2007-187446 | A | 7/2007 |
| JP | 2008209338 | A | 9/2008 |
| JP | 2009036512 | A | 2/2009 |
| JP | 2009168730 | A | 7/2009 |
| JP | 2009168730 | A * | 7/2009 |
| JP | 2010-101910 | A | 5/2010 |
| JP | 2010190641 | A | 9/2010 |
| JP | 2011149747 | A | 8/2011 |
| JP | 2013185975 | A | 9/2013 |
| JP | 2014-142556 | A | 8/2014 |
| JP | 2018-36721 | A | 3/2018 |

OTHER PUBLICATIONS

Decision of Refusal dated Jun. 30, 2020 in a counterpart Japanese patent application No. 2018-225370.
Japanese Office Action dated Feb. 25, 2020 in a counterpart Japanese patent application No. 2018-225370.
Japanese Office Action dated Jun. 7, 2022 in Japanese patent application No. 2020-159933.
A Communication pursuant to Article 94(3) EPC dated May 13, 2022 in European patent application No. 19212135.8.

* cited by examiner

EMBODIMENT 1

FIG. 6A  TIME QC
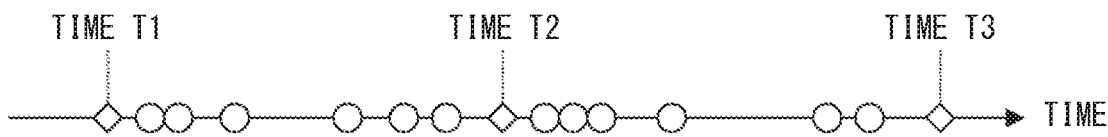
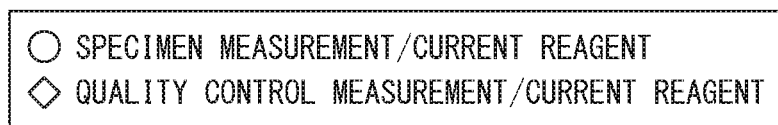
FIG. 6B  TIME INTERVAL QC
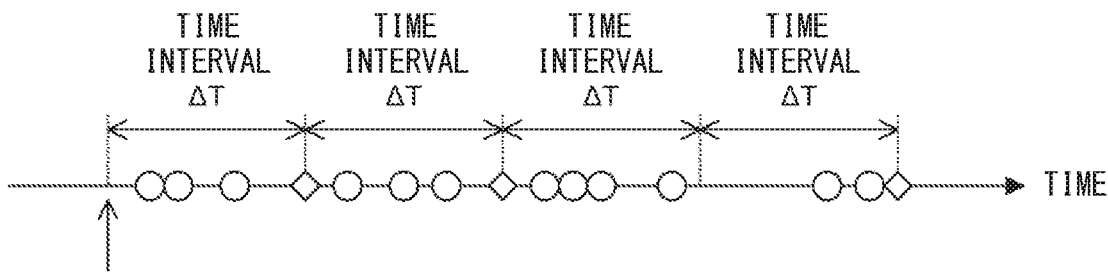
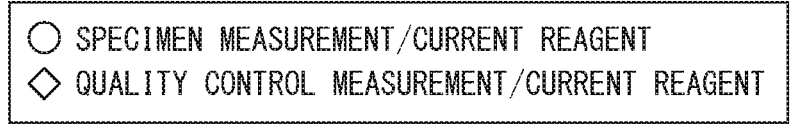
FIG. 6C  TEST NUMBER QC
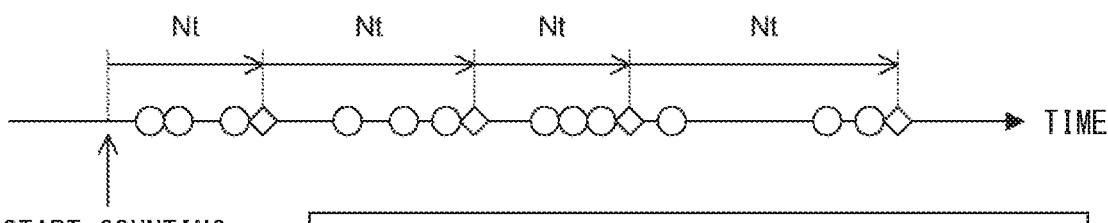
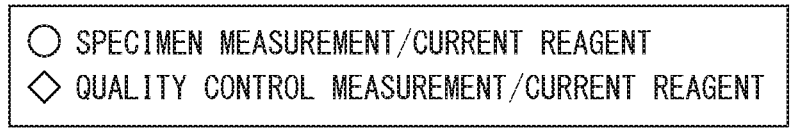

FIG. 7A  VIAL QC
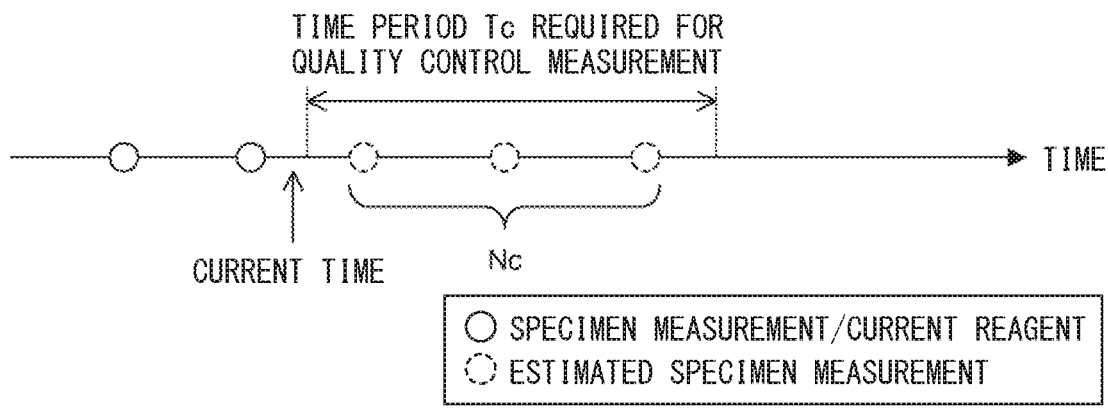
FIG. 7B
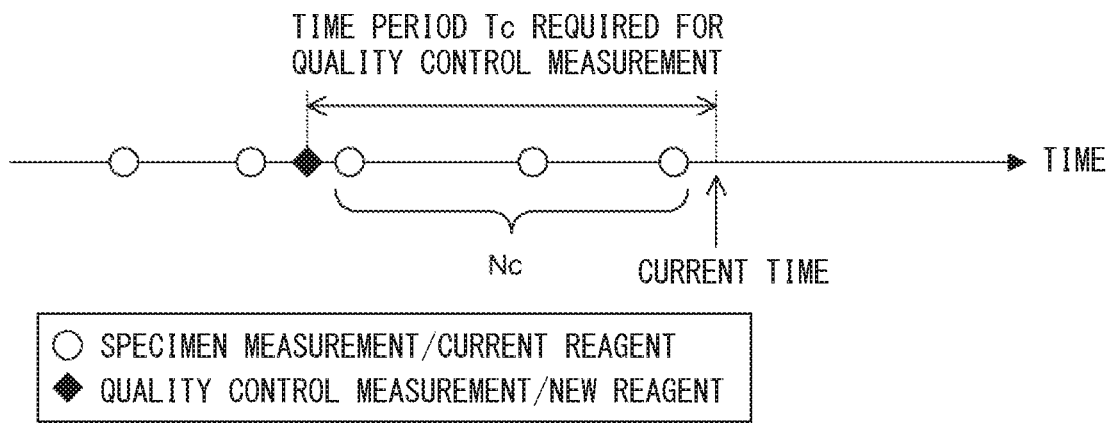
FIG. 7C
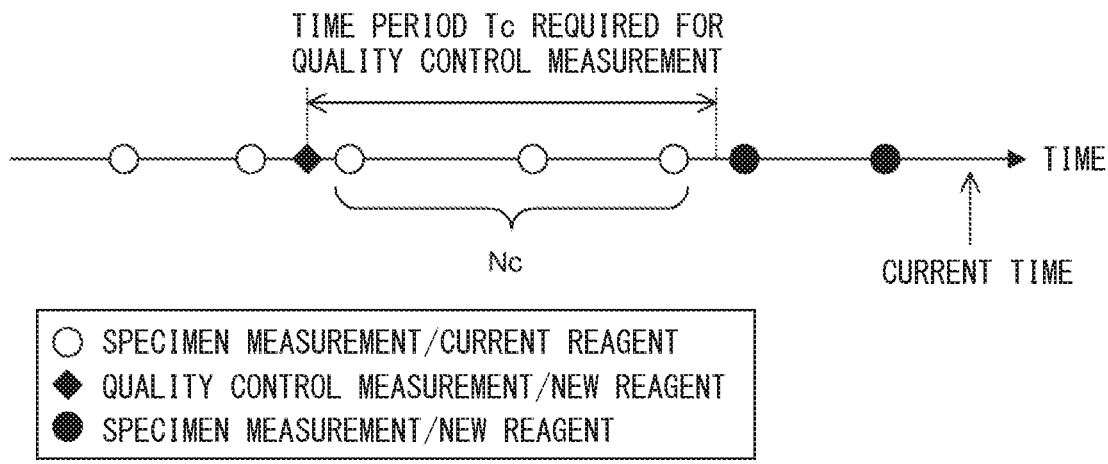

FIG. 8A  VIAL QC (COMPARATIVE EXAMPLE)
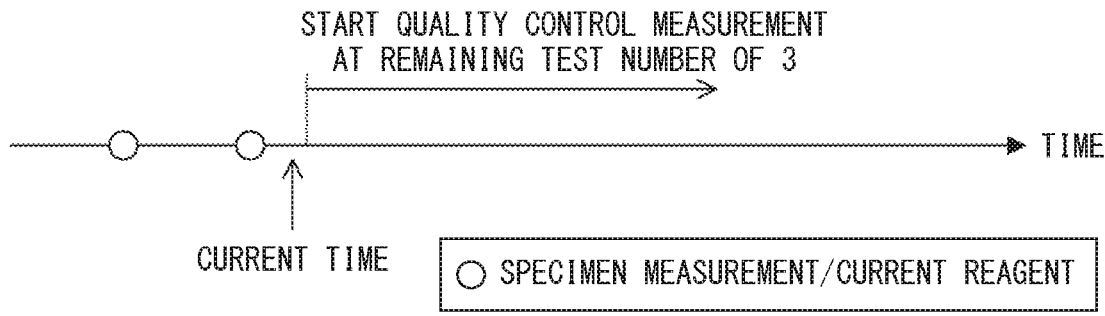
FIG. 8B  VIAL QC (COMPARATIVE EXAMPLE)
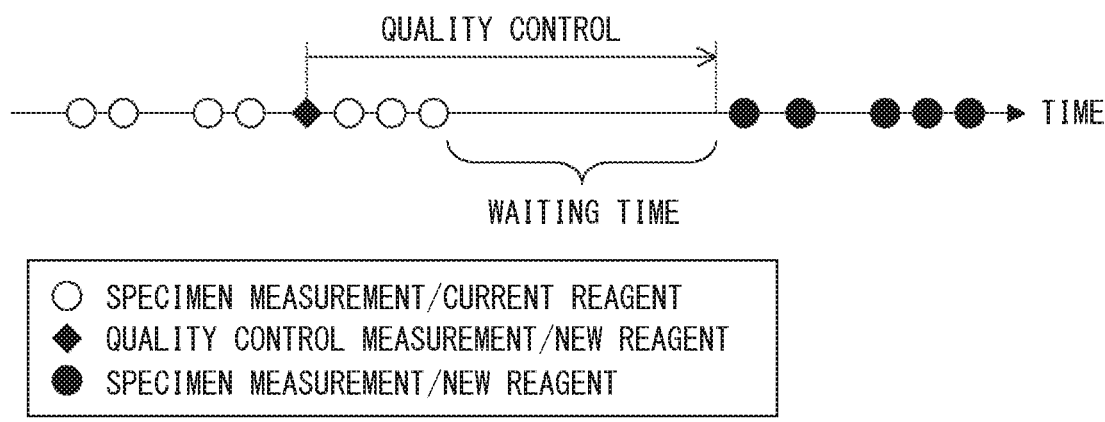
FIG. 8C  VIAL QC (COMPARATIVE EXAMPLE)
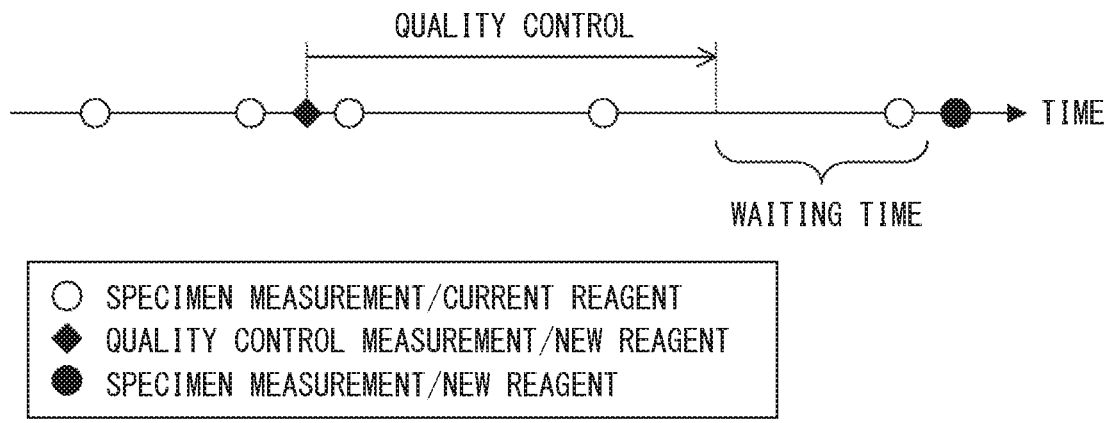

FIG. 9A

| MEASUREMENT ITEM | ITEM | VALUE |
|---|---|---|
| PT | ELAPSED TIME IN TIME INTERVAL QC | ...HOUR...MINUTE...SECOND |
| | TEST NUMBER IN TEST NUMBER QC | TIMES |
| APTT | ELAPSED TIME IN TIME INTERVAL QC | ...HOUR...MINUTE...SECOND |
| | TEST NUMBER IN TEST NUMBER QC | TIMES |

FIG. 9B

| SPECIMEN NUMBER | START DATE | START TIME | END TIME | MEASUREMENT ITEM |
|---|---|---|---|---|
| 0001 | 2018/10/30 | 11:10 | 11:18 | PT,APTT |
| 0002 | 2018/10/30 | 11:11 | 11:19 | PT,APTT |
| 0003 | 2018/10/30 | 11:12 | 11:20 | PT,APTT |
| 0004 | 2018/10/30 | 11:13 | 11:21 | PT,Fbg |
| 0005 | 2018/10/30 | 11:14 | 11:22 | PT,Fbg |

FIG. 9C

MEASUREMENT ITEM: PT

| TIME FRAME | MONDAY | TUESDAY | WEDNESDAY | THURSDAY | FRIDAY | |
|---|---|---|---|---|---|---|
| 6 | ... | ... | ... | ... | ... | |
| 7 | ... | ... | ... | ... | ... | |
| 8 | ... | ... | ... | ... | ... | |
| 9 | ... | ... | ... | ... | ... | |
| 10 | ... | ... | ... | ... | ... | |

FIG. 11

| MEASUREMENT ITEM | TIME QC | TIME | TIME INTERVAL QC | TIME INTERVAL | TEST NUMBER QC | TEST NUMBER | VIAL QC |
|---|---|---|---|---|---|---|---|
| APTT-FSL | ON | 9:00 | OFF | 8 | OFF | 120 | ON |
| APL | ON | 10:00 | OFF | 6 | OFF | 150 | OFF |
| AT3 | OFF | 9:00 | ON | 8 | OFF | 200 | ON |
| Plg | OFF | 10:00 | OFF | 8 | ON | 190 | ON |
| PC | OFF | 10:00 | ON | 7 | OFF | 160 | OFF |
| DD wide | OFF | 9:00 | OFF | 6 | ON | 250 | OFF |
| XIII ch | OFF | 10:00 | ON | 5 | OFF | 230 | OFF |
| VII | ON | 9:00 | OFF | 8 | OFF | 210 | ON |
| VIII-FSL | OFF | 9:00 | OFF | 7 | ON | 150 | OFF |
| Fbg | OFF | 10:00 | OFF | 8 | ON | 110 | OFF |

402a — MEASUREMENT ITEM column
402b — EDIT ITEM button
402

FIG. 17A
FIG. 17B
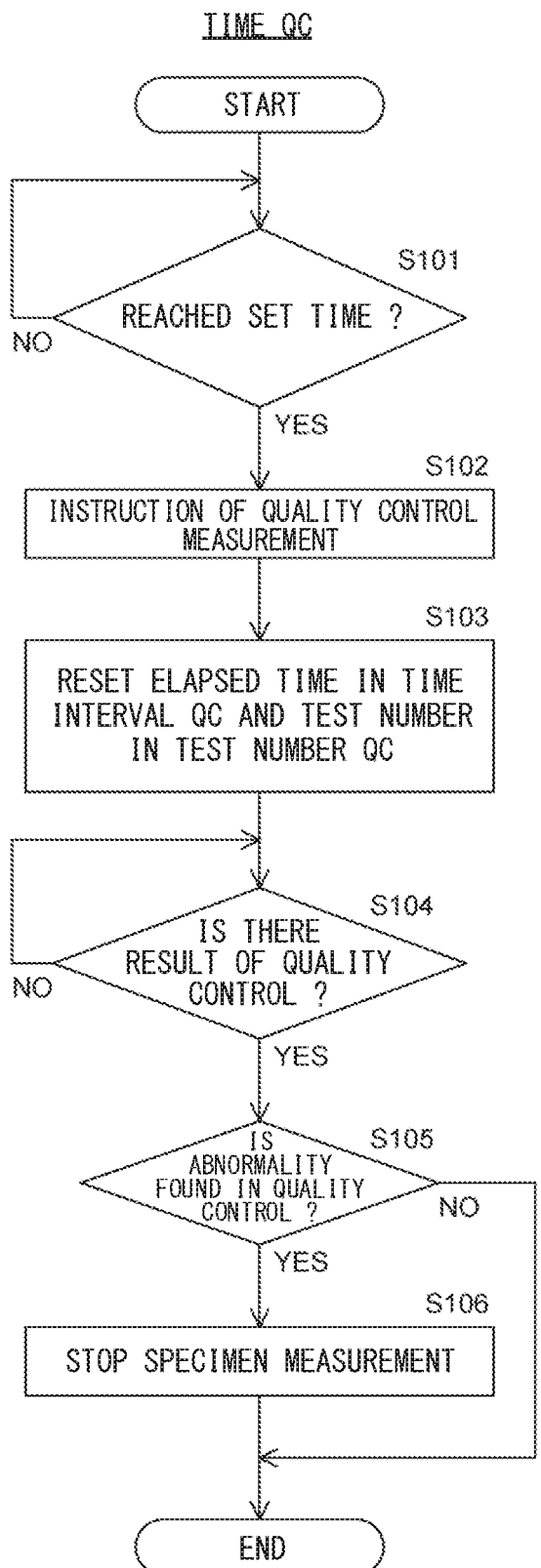
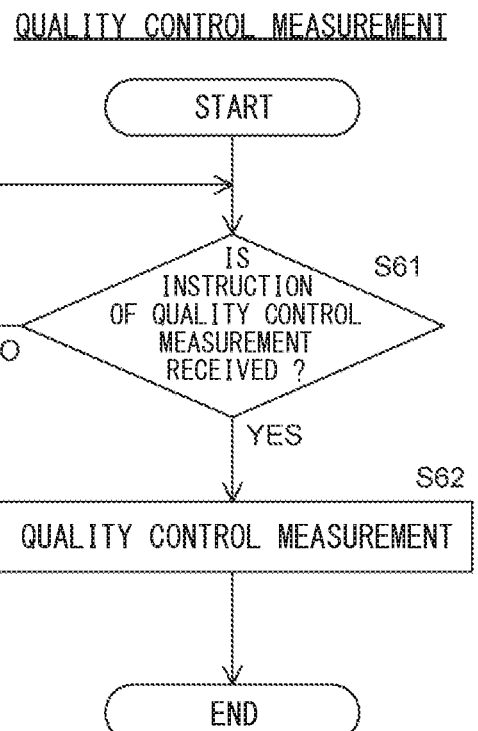

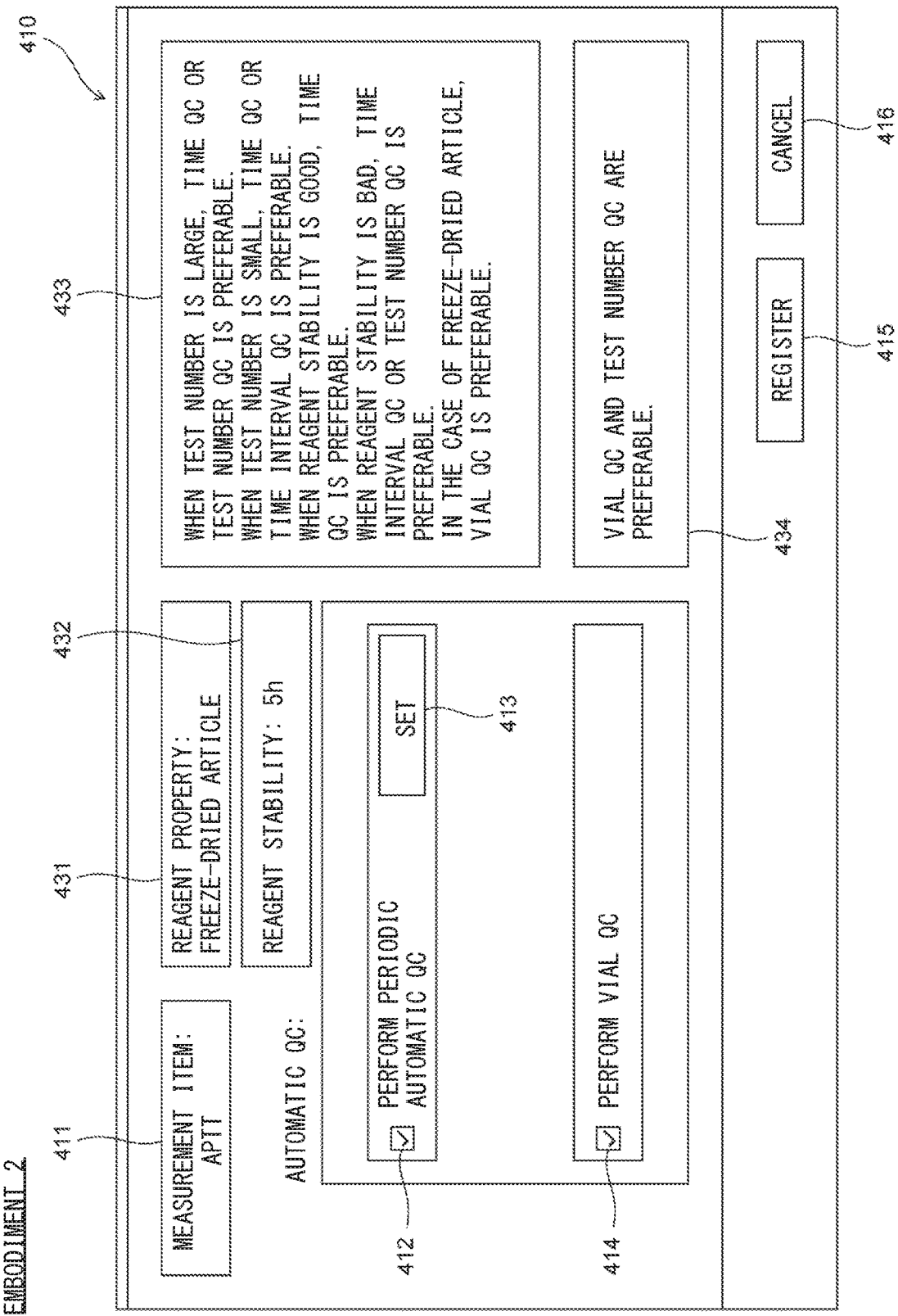

FIG. 21A

|  |  | TEST NUMBER | |
|---|---|---|---|
|  |  | SMALL | LARGE |
| REAGENT STABILITY | GOOD | TIME QC | TIME QC |
|  | BAD | TIME INTERVAL QC | TEST NUMBER QC |

FIG. 21B

| REAGENT PROPERTY | |
|---|---|
| FREEZE-DRIED ARTICLE | LIQUID-STATE ARTICLE |
| VIAL QC | — |

SPECIMEN ANALYZER AND SPECIMEN ANALYSIS METHOD

RELATED APPLICATIONS

This application claims priority to Japanese Patent Application No. 2018-225370 filed on Nov. 30, 2018, the entire content of which is incorporated herein by reference.

BACKGROUND OF THE INVENTION

1. Field of the Invention

The present invention relates to a specimen analyzer and a specimen analysis method.

2. Description of the Related Art

Specimen analyzers are known that control the quality of a reagent by measuring a measurement sample prepared by mixing the reagent with a quality control substance of which components are known. Japanese Laid-Open Patent Publication No. 2010-190641 describes a quality control method that is performed on a reagent in a new reagent container when the remaining amount of a reagent in a reagent container has become small, and a quality control method that is performed at a certain time interval on a reagent in a reagent container in use.

SUMMARY OF THE INVENTION

The scope of the present invention is defined solely by the appended claims, and is not affected to any degree by the statements within this summary.

In the specimen analyzer described above, a quality control measurement is performed at a certain time interval only, except for the timing at which a reagent container is replaced. Thus, the frequency of performing the quality control measurement cannot be flexibly set. However, at facilities and the like where specimen analysis is performed with use of a specimen analyzer, it is desired to perform the quality control measurement at an appropriate frequency in accordance with the execution frequency of specimen measurements, reagent information, and the like.

A first aspect of the present invention relates to a specimen analyzer configured to perform analysis on a specimen for a plurality of measurement items. A specimen analyzer (30) according to the present aspect includes a measurement section (32) configured to perform a specimen measurement for measuring a measurement sample prepared from the specimen and a reagent corresponding to a measurement item, and configured to perform a quality control measurement for measuring a measurement sample prepared from a quality control substance and a reagent corresponding to a measurement item; and a controller (331) programmed to set a quality control for each measurement item, from a quality control group that includes at least two types of quality controls selected from a first quality control in which the quality control measurement is performed at a predetermined time, a second quality control in which the quality control measurement is performed every time the specimen measurement is performed a predetermined number of times, and a third quality control in which the quality control measurement is performed every predetermined time interval. The controller (331) is programmed to control the measurement section (32) in accordance with the set quality control.

According to the specimen analyzer of the present aspect, at least one quality control can be set from a plurality of quality controls having different execution frequencies of the quality control measurement. Thus, if a quality control can be set from a quality control group including a plurality of quality controls, the quality control measurement can be performed at an appropriate frequency in accordance with the execution frequency of the specimen measurement, reagent information, and the like. When the first quality control is set, for example, in a case where reagent stability is high, unnecessary quality control measurements can be inhibited from being performed. When the second quality control is set, for example, in a case where the execution frequency of the specimen measurement is high, the quality control measurement can be assuredly performed. When the third quality control is set, for example, in a case where the execution frequency of the specimen measurement is low, unnecessary quality control measurements can be inhibited from being performed.

In the specimen analyzer (30) according to the present aspect, the controller (331) may be programmed to receive a measurement item and set a quality control for the received measurement item. Accordingly, an appropriate quality control can be set for each measurement item.

In the specimen analyzer (30) according to the present aspect, when the first quality control, the second quality control, and the third quality control are set, the measurement section (32) may prepare a measurement sample from the quality control substance and a reagent contained in a reagent container (21) currently used, and perform the quality control measurement.

In the specimen analyzer (30) according to the present aspect, the measurement section (32) may include a reagent dispensing unit (270) configured to open a cap portion (261) covering an opening (21b) of a reagent container (21) and dispense a reagent contained in the reagent container (21) when the measurement sample is prepared. If the cap portion which covers the opening of a reagent container is opened in this manner every time preparation of a measurement sample is performed, degradation of the reagent contained in the reagent container could be advanced in accordance with the number of times of opening/closing of the cap portion. In contrast, according to the specimen analyzer of the present aspect, when the second quality control is set, for example, the quality control measurement is performed in accordance with the number of times of specimen measurement, and thus, degradation of the reagent can be quickly understood.

In the specimen analyzer (30) according to the present aspect, the measurement section (32) may include a light source part (292) configured to apply light to each measurement sample; and a light receiver (293) configured to receive light that has been generated from the measurement sample. The specimen measurement and the quality control measurement may each be a measurement related to blood coagulation.

In the specimen analyzer (30) according to the present aspect, either one of the second quality control and the third quality control may be allowed to be alternatively set. The quality control measurement based on the second quality control and the quality control measurement based on the third quality control are each performed at a substantially constant interval. Therefore, if either one of them is performed, a necessary quality control can be performed. According to the specimen analyzer of the present aspect, either one of the second quality control and the third quality control can be alternatively set. Thus, unnecessary quality controls can be inhibited from being performed, and consumption of quality control substances and reagents can be suppressed. In addition, since setting of unnecessary quality controls can be avoided, the setting operation by the operator can be simplified.

In the specimen analyzer (30) according to the present aspect, the controller (331) may be programmed to reset a count of a number of times of measurement according to the second quality control when the quality control measurement has been performed on the basis of the first quality control. The quality control measurement is performed at temporal intervals so as to ensure the accuracy of specimen measurements. Thus, the necessity of performing a plurality of quality control measurements at close timings is low. According to the specimen analyzer of the present aspect, when the quality control measurement based on the first quality control is performed, the count of the elapsed time in the second quality control is reset. Accordingly, it is possible to inhibit the quality control measurement based on the second quality control from being performed at a close timing, after a quality control measurement is performed at a predetermined time. In addition, unnecessary quality controls are inhibited from being performed, and thus, consumption of quality control substances and reagents can be suppressed.

In the specimen analyzer (30) according to the present aspect, the controller (331) may be programmed to reset a count of an elapsed time in the third quality control when the quality control measurement has been performed on the basis of the first quality control. The quality control measurement is performed at temporal intervals so as to ensure the accuracy of specimen measurements. Thus, the necessity of performing a plurality of quality control measurements at close timings is low. According to the specimen analyzer of the present aspect, when the quality control measurement based on the first quality control is performed, the count of the number of times of measurement according to the third quality control is reset. Accordingly, it is possible to inhibit the quality control measurement based on the third quality control from being performed at close timings after a quality control measurement has been performed at a predetermined time. In addition, unnecessary quality controls are inhibited from being performed, and thus, consumption of quality control substances and reagents can be suppressed.

In the specimen analyzer (30) according to the present aspect, the quality control group may further include a fourth quality control in which, when a remaining amount of a reagent in a first reagent container (21) has become smaller than a predetermined amount, the quality control measurement is performed on the basis of a reagent in a second reagent container (21) containing a reagent of the same type.

In this case, the controller (331) may be programmed to estimate a number of times of the specimen measurement executable in a time period required for the quality control measurement, and programmed to calculate, as the predetermined amount, a reagent amount necessary for the specimen measurement to be performed the estimated number of times. Accordingly, the specimen measurement that uses the reagent in the first reagent container and that is performed in the time period required for the quality control measurement can be performed while the quality control measurement using the reagent in the second reagent container is being performed. Thus, it is possible to easily avoid a situation where execution of a specimen measurement using the reagent in the second reagent container is caused to wait until the end of the quality control measurement. Therefore, a specimen measurement using the reagent in the second reagent container can be quickly started after the specimen measurement using the reagent in the first reagent container. In addition, it is possible to easily avoid a situation where, after a quality control measurement has ended, execution of a specimen measurement using the reagent in the second reagent container is caused to wait until there is no remaining reagent in the first reagent container. Therefore, the quality of the new reagent can be ensured on the basis of the result of the quality control regarding the new reagent.

In this case, the specimen analyzer (30) according to the present aspect may include a storage unit (332) configured to store history information regarding past execution history of the specimen measurement performed by the measurement section (32), and the controller (331) may be programmed to estimate the number of times on the basis of the history information. Accordingly, the number of times of specimen measurement executable in the time period required for the quality control measurement can be accurately estimated.

In this case, the number of times may be a number of times of the specimen measurement predicted to be performed in a day of a week or a time frame to which a current time belongs. When the number of times of specimen measurement predicted to be performed in a day of week and a time frame to which the current time belongs is obtained on the basis of history information in this manner, the reagent amount necessary for specimen measurements to be performed in a time period required for a quality control measurement can be appropriately estimated.

The specimen analyzer (30) according to the present aspect may include a display unit (333), and the controller (331) may be programmed to cause the display unit (333) to display a reception screen (410, 420) for receiving a setting of each quality control included in the quality control group, and may be programmed to set a quality control received through the reception screen (410, 420), as a quality control to be performed. Accordingly, the operator can easily set each quality control included in the quality control group through the reception screen.

In this case, the controller (331) may be programmed to cause the display unit (333) to display, for each measurement item, recommendation information that suggests which of the quality controls in the quality control group is preferable. Accordingly, the operator can visually understand which quality control in the quality control group is preferably performed, by referring to the recommendation information.

In this case, the specimen analyzer (30) according to the present aspect may include a storage unit (332) configured to store history information regarding past execution history of the specimen measurement performed by the measurement section (32), and the controller (331) may be programmed to cause the display unit (333) to display the recommendation information on the basis of the history information.

In this case, the controller (331) may be programmed to predict an execution frequency of the specimen measurement on the basis of the history information; cause, when the execution frequency is greater than an execution frequency threshold, the recommendation information to include an indication that the second quality control is preferable; and cause, when the execution frequency is smaller than the execution frequency threshold, the recommendation information to include an indication that the third quality control is preferable. Accordingly, which of the second quality control and the third quality control is preferable is appropriately determined in accordance with the magnitude of the execution frequency. Thus, a preferable quality control can be appropriately displayed as recommendation information.

In the specimen analyzer (30) according to the present aspect, the controller (331) may be programmed to cause the display unit (333) to display the recommendation information on the basis of reagent information. The operator can determine a preferable quality control in the quality control group by referring to the recommendation information based on the reagent information.

In this case, the controller (331) may be programmed to cause, when a value indicating reagent stability is greater than a reagent stability threshold, the recommendation information to include an indication that the first quality control is preferable. Accordingly, the operator can visually understand that the first quality control is preferable when the reagent stability is high.

The quality control group may further include a fourth quality control in which, when a remaining amount of a reagent in a first reagent container (21) has become smaller than a predetermined amount, the quality control measurement is performed on the basis of a reagent in a second reagent container (21) containing a reagent of the same type. The controller (331) may be programmed to cause, when reagent property corresponds to a freeze-dried article, the recommendation information to include an indication that the fourth quality control is preferable. Accordingly, when the reagent is a freeze-dried article, the operator can visually understand that the fourth quality control is preferable.

In the specimen analyzer (30) according to the present aspect, the controller (331) may be programmed to select, for each measurement item, a candidate quality control to be performed from among the quality controls included in the quality control group. Thus, when a candidate quality control to be performed is selected, the operator can save the trouble of determining which quality control should be performed.

In this case, the specimen analyzer may include a storage unit (332) configured to store history information regarding past execution history of the specimen measurement performed by the measurement section (32). The controller (331) may be programmed to predict an execution frequency of the specimen measurement for each measurement item on the basis of the history information, and programmed to select the candidate quality control to be performed on the basis of the predicted execution frequency.

In this case, the controller (331) may be programmed to select, when the execution frequency is greater than an execution frequency threshold, at least the second quality control as a candidate quality control to be performed; and select, when the execution frequency is smaller than the execution frequency threshold, at least the third quality control as a candidate quality control to be performed. Accordingly, either one of the second quality control and the third quality control is selected at least as a candidate quality control to be performed, in accordance with the magnitude of the execution frequency. Thus, the operator can save the trouble of selecting a quality control in consideration of the execution frequency.

In the specimen analyzer (30) according to the present aspect, the controller (331) may be programmed to select the candidate quality control to be performed, on the basis of reagent information.

In this case, the controller (331) may be programmed to select, when a value indicating reagent stability is greater than a reagent stability threshold, at least the first quality control as the candidate quality control to be performed. Accordingly, when the reagent stability is high, the first quality control is selected. Thus, the operator can save the trouble of selecting the first quality control after determining that the reagent stability is high.

The quality control group may further include a fourth quality control in which, when a remaining amount of a reagent in a first reagent container (21) has become smaller than a predetermined amount, the quality control measurement is performed on the basis of a reagent in a second reagent container (21) containing a reagent of the same type. The controller (331) may be programmed to select, when reagent property corresponds to a freeze-dried article, the fourth quality control as the candidate quality control to be performed. Accordingly, when the reagent property corresponds to a freeze-dried article, the fourth quality control is selected. Thus, the operator can save the trouble of selecting the fourth quality control after determining that the reagent property corresponds to a freeze-dried article.

The specimen analyzer (30) according to the present aspect may include a display unit (333). The controller (331) may be programmed to cause the display unit (333) to display a reception screen (410, 420) for receiving a setting of a quality control to be performed among quality controls selected as candidate quality controls to be performed. Accordingly, with respect to the quality control selected by the controller as the candidate quality control to be performed, the operator can smoothly input settings such as whether or not to perform the quality control, specific parameters, etc.

In the specimen analyzer (30) according to the present aspect, the controller (331) may be programmed to set, as a quality control to be performed, a quality control selected as a candidate quality control to be performed. Accordingly, the quality control to be performed is automatically set. Thus, the operator can save the trouble of setting a quality control to be performed on the basis of the candidate quality control to be performed.

A second aspect of the present invention relates to a specimen analyzer configured to perform analysis on a specimen for a plurality of measurement items. The specimen analyzer (30) according to the present aspect includes a measurement section (32) configured to perform a specimen measurement for measuring a measurement sample prepared from the specimen and a reagent corresponding to a measurement item, and configured to perform a quality control measurement for measuring a measurement sample prepared from a quality control substance and a reagent corresponding to a measurement item; and a controller (331) programmed to set a quality control for each measurement item, from a quality control group that includes a quality control in which the quality control measurement is performed at a timing based on a first rule, and a quality control in which the quality control measurement is performed at a timing based on a second rule different from the first rule. The controller (331) is programmed to control the measurement section (32) in accordance with the set quality control.

According to the specimen analyzer of the present aspect, a quality control can be set from a quality control in which the quality control measurement is performed at a timing based on a first rule and a quality control in which the quality control is performed at a timing based on a second rule. That is, at least one quality control can be set from a plurality of quality controls that have different execution frequencies of the quality control measurement. Therefore, according to the specimen analyzer of the present aspect, effects similar to those of the first aspect are exhibited.

In the specimen analyzer (30) according to the present aspect, when the quality control is set, the measurement section (32) may prepare a measurement sample from the quality control substance and a reagent contained in a reagent container (21) currently used, and perform the quality control measurement.

In the specimen analyzer (30) according to the present aspect, the quality control group may further include another quality control in which, when a remaining amount of a reagent in a first reagent container (21) has become smaller than a predetermined amount, the quality control measurement is performed on the basis of a reagent in a second reagent container (21) containing a reagent of the same type.

A third aspect of the present invention relates to a specimen analysis method for performing analysis on a specimen for a plurality of measurement items. The specimen analysis method according to the present aspect includes performing a specimen measurement for measuring a measurement sample prepared from the specimen and a reagent corresponding to a measurement item; performing a quality control measurement for measuring a measurement sample prepared from a quality control substance and a reagent corresponding to a measurement item; and setting a quality control for each measurement item, from a quality control group that includes at least two types of quality controls selected from a first quality control in which the quality control measurement is performed at a predetermined time, a second quality control in which the quality control measurement is performed every time the specimen measurement is performed a predetermined number of times of measurement, and a third quality control in which the quality control measurement is performed every predetermined time interval.

According to the specimen analysis method of the present aspect, effects similar to those of the first aspect are exhibited.

In the specimen analysis method according to the present aspect, the setting may include receiving a measurement item and setting a quality control for the received measurement item.

In the specimen analysis method according to the present aspect, the performing of the quality control measurement may include, when the first quality control, the second quality control, and the third quality control are set, preparing a measurement sample from the quality control substance and a reagent contained in a reagent container (21) currently used, and performing the quality control measurement.

In the specimen analysis method according to the present aspect, the performing of the specimen measurement may include opening a cap portion (261) that covers an opening (21b) of a reagent container (21) and dispensing a reagent contained in the reagent container (21) when the measurement sample is prepared.

In the specimen analysis method according to the present aspect, the performing of the specimen measurement and the performing of the quality control measurement may each include applying light to each measurement sample and receiving light that has been generated from the measurement sample. The specimen measurement and the quality control measurement may each be a measurement related to blood coagulation.

In the specimen analysis method according to the present aspect, the quality control group may further include a fourth quality control in which, when a remaining amount of a reagent in a first reagent container (21) has become smaller than a predetermined amount, the quality control measurement is performed on the basis of a reagent in a second reagent container (21) containing a reagent of the same type.

In this case, the specimen analysis method according to the present aspect may include estimating a number of times of the specimen measurement executable in a time period required for the quality control measurement; and calculating, as the predetermined amount, a reagent amount necessary for the specimen measurement to be performed the estimated number of times.

The specimen analysis method according to the present aspect may include displaying, for each measurement item, recommendation information that suggests which of the quality controls in the quality control group is preferable.

The specimen analysis method according to the present aspect may include selecting, for each measurement item, a candidate quality control to be performed from among the quality controls included in the quality control group.

A fourth aspect of the present invention relates to a specimen analysis method for performing analysis on a specimen for a plurality of measurement items. The specimen analysis method according to the present aspect includes performing a specimen measurement for measuring a measurement sample prepared from the specimen and a reagent corresponding to a measurement item; performing a quality control measurement for measuring a measurement sample prepared from a quality control substance and a reagent corresponding to a measurement item; and setting a quality control for each measurement item, from a quality control group that includes a quality control in which the quality control measurement is performed at a timing based on a first rule, and a quality control in which the quality control measurement is performed at a timing based on a second rule different from the first rule.

According to the specimen analysis method of the present aspect, effects similar to those of the second aspect are exhibited.

In the specimen analysis method according to the present aspect, the performing of the quality control measurement may include, when the quality control is set, preparing a measurement sample from the quality control substance and a reagent contained in a reagent container (21) currently used, and performing the quality control measurement.

In the specimen analysis method according to the present aspect, the quality control group may further include another quality control in which, when a remaining amount of a reagent in a first reagent container (21) has become smaller than a predetermined amount, the quality control measurement is performed on the basis of a reagent in a second reagent container (21) containing a reagent of the same type.

BRIEF DESCRIPTION OF THE DRAWINGS

FIG. 6A is a schematic diagram for describing quality control measurements performed in a time QC according to Embodiment 1;

FIG. 6B is a schematic diagram for describing quality control measurements performed in a time interval QC according to Embodiment 1;

FIG. 6C is a schematic diagram for describing quality control measurements performed in a test number QC according to Embodiment 1;

FIG. 7A is a schematic diagram for describing a vial QC according to Embodiment 1;

FIG. 7B is a schematic diagram for describing the vial QC according to Embodiment 1;

FIG. 7C is a schematic diagram for describing the vial QC according to Embodiment 1;

FIG. 8A is a schematic diagram for describing a vial QC according to a comparative example.

FIG. 8B is a schematic diagram for describing the vial QC according to the comparative example.

FIG. 8C is a schematic diagram for describing the vial QC according to the comparative example.

FIG. 9A is a conceptual diagram showing elapsed time in the time interval QC and test number in the test number QC stored in a storage unit according to Embodiment 1;

FIG. 9B is a conceptual diagram showing history information stored in the storage unit according to Embodiment 1;

FIG. 9C is a conceptual diagram showing the number of times of specimen measurement in each time frame of each day of week generated on the basis of history information according to Embodiment 1;

FIG. 11 is a schematic diagram showing a configuration of an edit measurement item selection screen displayed on the display unit according to Embodiment 1;

FIG. 17A is a flow chart showing a process of the time QC according to Embodiment 1;

FIG. 17B is a flow chart showing a process of a quality control measurement according to Embodiment 1;

FIG. 20 is a schematic diagram showing a configuration of a reception screen displayed on a display unit according to Embodiment 2;

FIG. 21A shows a quality control determined on the basis of the test number and reagent stability according to Embodiment 2;

FIG. 21B shows a quality control determined on the basis of reagent property according to Embodiment 2;

DETAILED DESCRIPTION OF THE PREFERRED EMBODIMENTS

Embodiment 1

Figure 1:
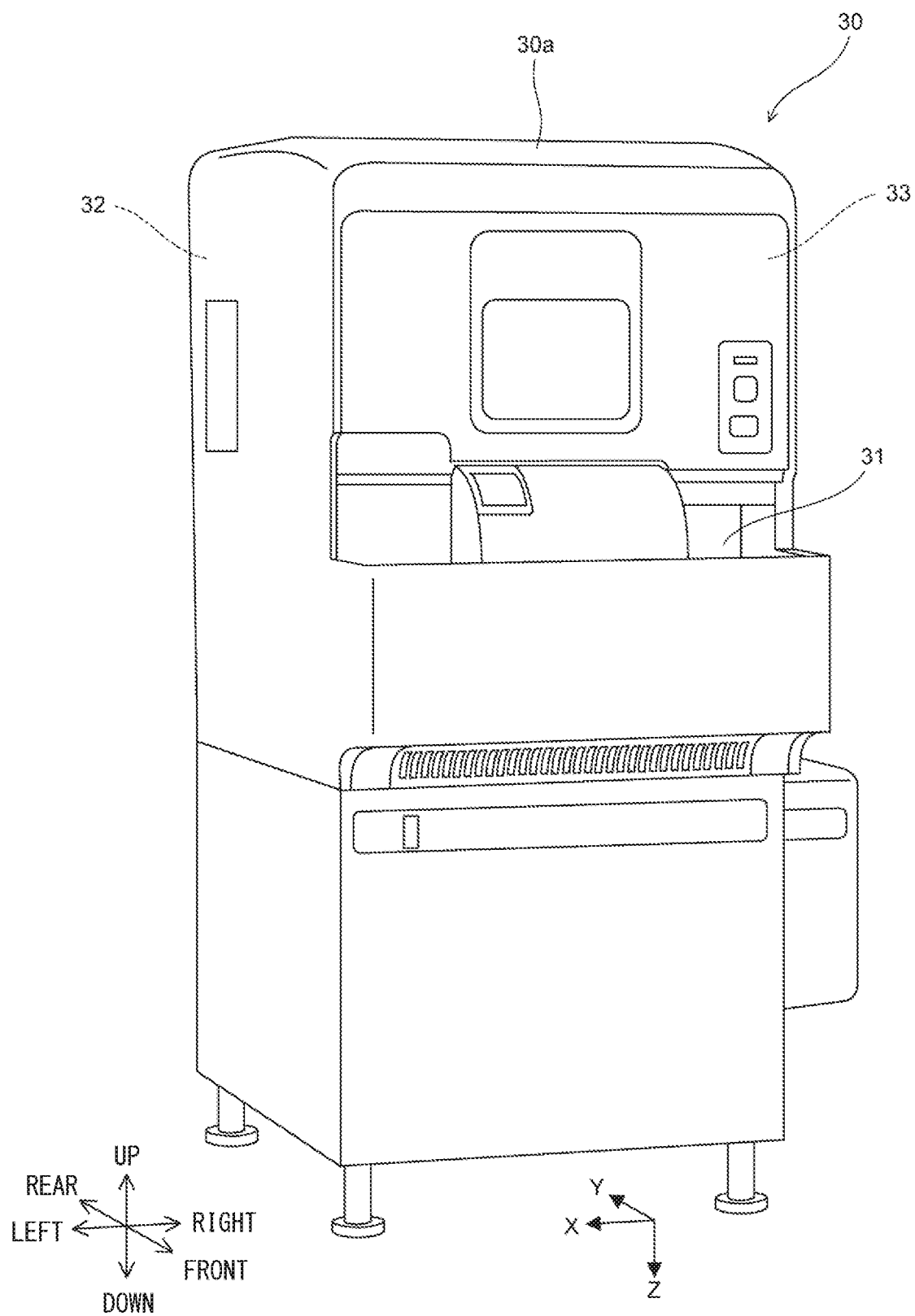
FIG. 1 is a perspective view showing a configuration of a specimen analyzer according to Embodiment 1.

FIG. 1 is a perspective view showing a configuration of a specimen analyzer 30. The specimen analyzer 30 performs specimen analysis. Inside a housing 30a, the specimen analyzer 30 includes a transport section 31, a measurement section 32 described in detail with reference to FIGS. 2 to 4, and an analysis section 33 described in detail with reference to FIG. 5. In FIG. 1, XYZ axes are orthogonal to one another, and the X axis direction and the Y axis direction correspond to directions that are parallel to the horizontal plane. The X axis positive direction corresponds to the left direction, the Y axis positive direction corresponds to the rear direction, and the Z axis positive direction corresponds to the vertically down direction.

The measurement section 32 mixes a specimen and a reagent together to prepare a measurement sample based on the specimen. The measurement section 32 successively performs a specimen measurement for measuring a measurement sample based on a specimen and transmits a measurement result of the specimen measurement to the analysis section 33. In addition, the measurement section 32 mixes a quality control substance and a reagent together to prepare a measurement sample based on the quality control substance. Then, the measurement section 32 performs a quality control measurement for measuring a measurement sample based on the quality control substance at a predetermined timing, and transmits a measurement result of the quality control measurement to the analysis section 33.

The quality control substance is also referred to as a control sample, and is a sample of which compositions are known. Therefore, if measurement conditions are the same, measurement results based on the quality control substance are the same. The quality control substance broadly encompasses substances prepared by extracting a predetermined component from a specimen collected from an animal, and artificially produced substances such as latex particles produced so as to be analogous to particles contained in a specimen.

The analysis section 33 performs specimen analysis on the basis of a measurement result of a specimen measurement, and performs analysis on whether or not a reagent is appropriate on the basis of a measurement result of a quality control measurement.

Here, in the specimen analyzer 30 of Embodiment 1, a plurality of quality controls having different start conditions of the quality control measurement are performed. Hereinafter, a plurality of quality controls performed in the specimen analyzer 30 will be referred to as a "quality control group". The quality control group includes at least two types of quality controls selected from a first quality control in which a quality control measurement is performed at a predetermined time; a second quality control in which a quality control measurement is performed every time specimen measurements are performed a predetermined number of times of measurement; and a third quality control in which a quality control measurement is performed every predetermined time interval. The analysis section 33 sets a quality control for each measurement item from the quality control group, and controls the measurement section 32 in accordance with the set quality control.

As described above, according to Embodiment 1, at least one quality control can be set from a quality control group that includes a plurality of quality controls having different execution frequencies of the quality control measurement. Thus, when a quality control can be set from a quality control group that includes a plurality of quality controls, the quality control measurement can be performed at an appropriate frequency in accordance with the execution frequency of specimen measurements, reagent information, and the like.

The control by the analysis section 33 described above is performed by a controller 331 of the analysis section 33 described later with reference to FIG. 5, but may be performed by another controller.

Figure 2:
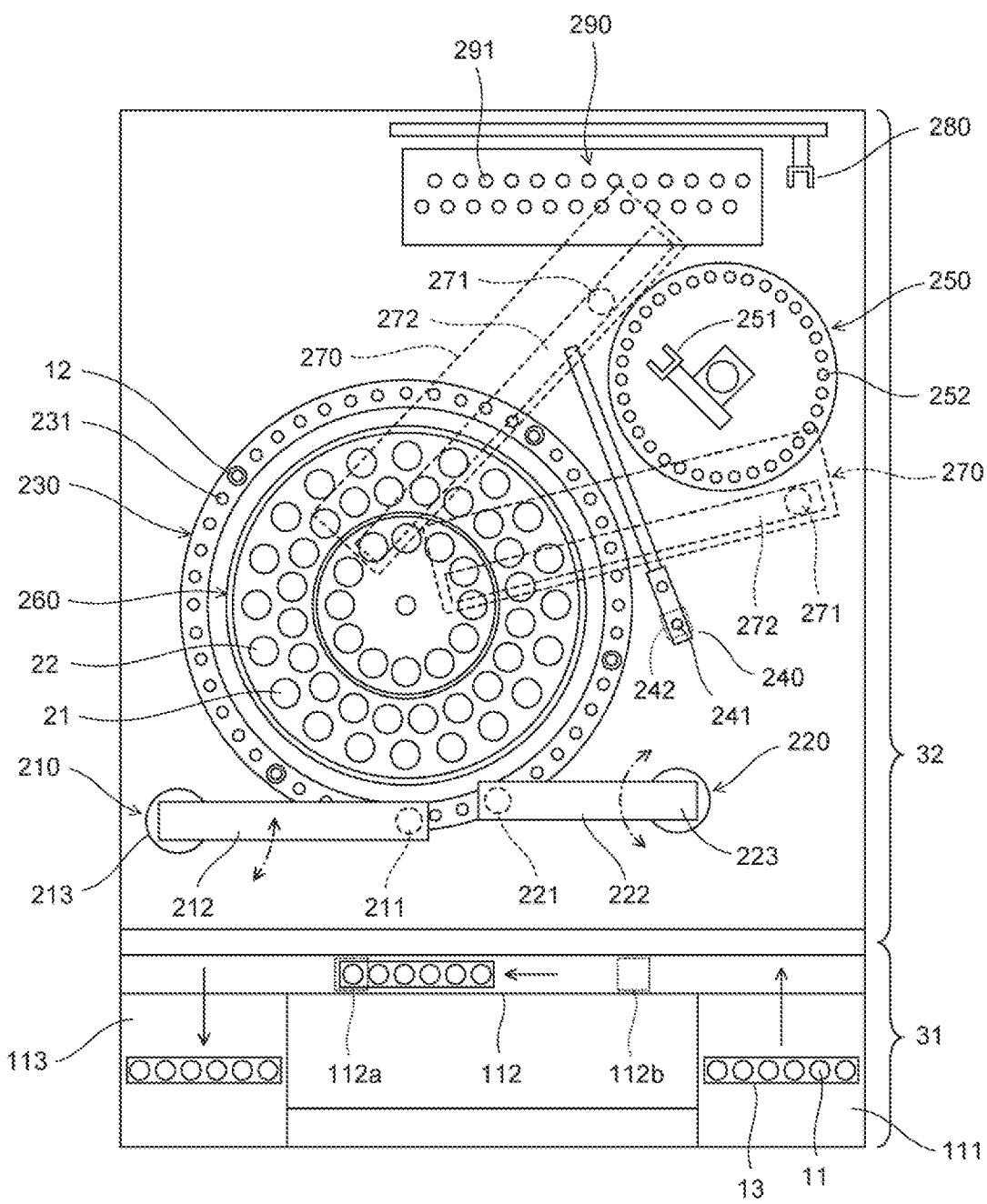
FIG. 2 is a schematic plan view of a configuration of a transport section and a measurement section according to Embodiment 1, viewed from above.

FIG. 2 is a schematic plan view of a configuration of the transport section 31 and the measurement section 32 viewed from above. The measurement section 32 is disposed rearward of the transport section 31. The measurement section 32 performs measurement related to a blood coagulation test. Therefore, in Embodiment 1, the specimen contained in a specimen container 11 is plasma.

The liquid contained as a specimen in a specimen container 11 is not limited to plasma. That is, without being limited to plasma, the specimen contained in a specimen container 11 may be whole blood, serum, urine, lymph, celomic fluid, or the like. For example, when a measurement related to a hemocyte test is performed on a specimen in the measurement section 32, the specimen can be whole blood. For example, when a measurement related to a blood coagulation test, an immunity test, or a biochemical test is performed on a specimen in the measurement section 32, the specimen can be plasma. For example, when a measurement related to an immunity test or a biochemical test is performed on a specimen in the measurement section 32, the specimen can be serum.

The transport section 31 includes a rack storage part 111, a rack transport part 112, and a rack collection part 113. The rack storage part 111 and the rack collection part 113 are connected to the right end and the left end of the rack transport part 112, respectively. The rack storage part 111 transfers a specimen rack 13 rearward, by pushing the front face of the specimen rack 13 by means of a sending-in member that is movable in the front-rear direction. The rack transport part 112 transfers the specimen rack 13 in the left direction by means of a belt that is movable in the left-right direction and that engages with the lower face of the specimen rack 13. The rack collection part 113 transfers the specimen rack 13 forward, by pushing the rear face of the specimen rack 13 by means of a sending-in member that is movable in the front-rear direction.

An operator sets, in the rack storage part 111, a specimen rack 13 having specimen containers 11 set therein. The transport section 31 sends the specimen rack 13 set in the rack storage part 111 to the right end of the rack transport part 112, by means of the sending-in member of the rack storage part 111. Subsequently, the transport section 31 transports the specimen rack 13 in the left direction by means of the belt of the rack transport part 112, and sequentially positions a specimen container 11 at a suction position 112a or a suction position 112b. The suction position 112a is a position at which a specimen dispensing unit 210 described later suctions a specimen. The suction position 112b is a position at which a specimen dispensing unit 220 described later suctions a specimen. When suction of a specimen from all the specimen containers 11 held in the specimen rack 13 has ended, the transport section 31 transports the specimen rack 13 to the rack collection part 113 by means of the belt of the rack transport part 112 and the sending-in member of the rack collection part 113.

The measurement section 32 includes the specimen dispensing units 210, 220, a reaction chamber table 230, a transfer unit 240, a heating table 250, a reagent table 260, two reagent dispensing units 270, a transfer unit 280, and a detection unit 290.

The specimen dispensing unit 210 includes a suction part 211, an arm 212, and a mechanism part 213. The suction part 211 is provided at the leading end of the arm 212. The suction part 211 is a nozzle. The mechanism part 213 is configured to cause the arm 212 to rotate in the circumferential direction and move in the up-down direction. Accordingly, the suction part 211 can move in the circumferential direction and in the up-down direction. The specimen dispensing unit 210 causes the suction part 211 to be lowered from above to a specimen container 11 positioned at the suction position 112a, thereby causing the suction part 211 to penetrate a plug body sealing the specimen container 11. Then, the specimen dispensing unit 210 suctions the specimen from the specimen container 11 via the suction part 211, and discharges the suctioned specimen into a new reaction chamber 12 held in a holding hole 231 of the reaction chamber table 230.

Similar to the specimen dispensing unit 210, the specimen dispensing unit 220 includes a suction part 221, an arm 222, and a mechanism part 223. The suction part 221 is provided at the leading end of the arm 222. The suction part 221 is a nozzle. The mechanism part 223 is configured to cause the arm 222 to rotate in the circumferential direction and move in the up-down direction. Accordingly, the suction part 221 can move in the circumferential direction and in the up-down direction. The specimen dispensing unit 220 suctions a specimen from a specimen container 11 positioned at the suction position 112b or from a reaction chamber 12 held in the reaction chamber table 230, and discharges the suctioned specimen into a new reaction chamber 12 held by the transfer unit 240. The specimen dispensing unit 220 suctions a quality control substance from a container 22 set on the reagent table 260, and discharges the suctioned quality control substance into a new reaction chamber 12 held by the transfer unit 240.

The reaction chamber table 230 has a ring shape in a plan view, and is disposed outside the reagent table 260. The reaction chamber table 230 is configured to be rotatable in the circumferential direction. The reaction chamber table 230 includes a plurality of holding holes 231 for holding reaction chambers 12.

The transfer unit 240 includes a holding hole 241 for holding a reaction chamber 12, and a configuration for transferring the holding hole 241 forward and backward. The transfer unit 240 holds a new reaction chamber 12 in the holding hole 241, and positions this reaction chamber 12 at a discharge position 242. The specimen dispensing unit 220 discharges a specimen into the reaction chamber 12 positioned at the discharge position 242. Here, one or more measurement items are set for one specimen, and the specimen suctioned from one specimen container 11 is discharged for each measurement item into a new reaction chamber 12 sequentially positioned at the discharge position 242. The transfer unit 240 transfers backward the reaction chamber 12 having a specimen discharged therein, to position the reaction chamber 12 at the vicinity on the left side of the heating table 250.

The heating table 250 includes a transfer unit 251 for transferring a reaction chamber 12, and a plurality of holding holes 252 each for holding a reaction chamber 12. The transfer unit 251 of the heating table 250 transfers the reaction chamber 12 positioned at the vicinity on the left side of the heating table 250 by the transfer unit 240, to a holding hole 252 of the heating table 250. The heating table 250 has a circular contour in a plan view, and is configured to be rotatable in the circumferential direction. The heating table 250 heats reaction chambers 12 set in holding holes 252 to 37° C.

The reagent table 260 is configured to be able to have set thereon a reagent container 21 containing a reagent to be used in a measurement related to a blood coagulation test. The reagent table 260 is configured to be rotatable in the circumferential direction. A plurality of reagent containers 21 each containing a reagent to be used in a measurement of a measurement item are set on the reagent table 260. That is, the reagent to be used for each measurement item is determined in advance, and a plurality of reagent containers 21 corresponding to the measurement items are set on the reagent table 260. In addition, a container 22 containing a quality control substance is set on the reagent table 260.

Each reagent dispensing unit 270 includes a suction part 271 and a mechanism part 272. The suction part 271 is provided with a liquid surface sensor 271a shown in FIG. 4. When the suction part 271 is lowered, the liquid surface sensor 271a detects that the leading end of the suction part 271 has come into contact with the liquid surface of the reagent in a reagent container 21. The mechanism part 272 includes stepping motors 272a, 272b shown in FIG. 4. The stepping motor 272a causes the suction part 271 to move in the horizontal direction so as to cross the reagent table 260. The stepping motor 272b causes the suction part 271 to move in the up-down direction. The two reagent dispensing units 270 are provided at the lower side of the upper face of the housing 30a.

The reagent dispensing unit 270 dispenses a reagent into a reaction chamber 12 heated at the heating table 250. When a reagent is to be dispensed, the transfer unit 251 or the transfer unit 280 takes out a reaction chamber 12 from a holding hole 252 of the heating table 250. Then, the reagent dispensing unit 270 suctions the reagent from a reagent container 21 via the suction part 271, and discharges the suctioned reagent into the reaction chamber 12 taken out from the holding hole 252. Accordingly, when a specimen is contained in the reaction chamber 12, the reagent is mixed with the specimen, whereby a measurement sample based on the specimen is prepared. When a quality control substance is contained in the reaction chamber 12, the reagent is mixed with the quality control substance, whereby a measurement sample based on the quality control substance is prepared.

Figure 3A:
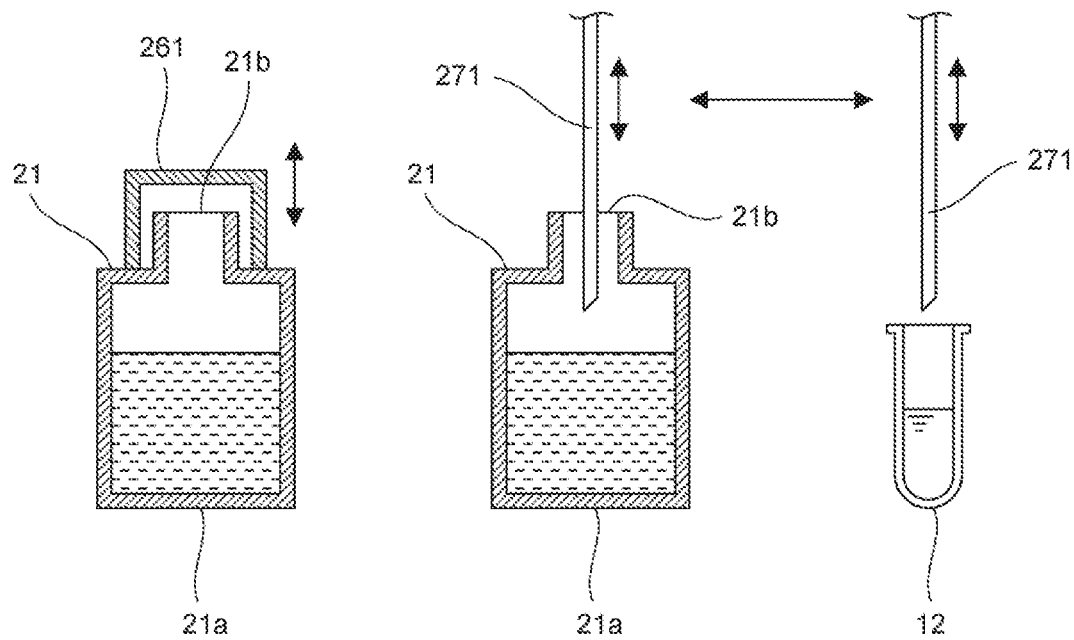
FIG. 3A is a schematic diagram for describing operation of dispensing a reagent in a reagent container into a reaction chamber according to Embodiment 1.

FIG. 3A is a schematic diagram for describing operation of dispensing a reagent in a reagent container 21 into a reaction chamber 12.

Each reagent container 21 has a trunk portion 21a containing a reagent, and an opening 21b which makes the upper end of the trunk portion 21a open to the outside. When setting an unopened reagent container 21 onto the reagent table 260, the operator removes the cap of the reagent container 21 provided at the opening 21b, and sets the reagent container 21 onto the reagent table 260, with the interior of the trunk portion 21a being open to the upper side through the opening 21b. Then, as shown in the leftmost drawing in FIG. 3A, a cap portion 261 provided at the reagent table 260 is placed over the upper end of the reagent container 21 so as to cover the opening 21b of the reagent container 21. The reagent table 260 includes an opening/closing mechanism 262 shown in FIG. 4. The opening/closing mechanism 262 opens/closes the opening 21b of a reagent container 21 by moving the cap portion 261.

When a reagent is suctioned from a reagent container 21, the cap portion 261 is withdrawn from the opening 21b by the opening/closing mechanism 262, whereby the upper side of the opening 21b is made open. Then, as shown in the center drawing in FIG. 3A, the suction part 271 is inserted into the trunk portion 21a by the stepping motors 272a, 272b of the reagent dispensing unit 270, and the reagent is suctioned by the suction part 271. Then, as shown in the rightmost drawing in FIG. 3A, the suction part 271 is inserted into a reaction chamber 12 by the stepping motors 272a, 272b, and the reagent suctioned by the suction part 271 is discharged into the reaction chamber 12. When suction of the reagent from the reagent container 21 ends, the cap portion 261 is placed over the upper end of the reagent container 21 by the opening/closing mechanism 262 so as to cover the opening 21b.

If the cap portion 261 which covers the opening 21b of a reagent container 21 is opened in this manner every time preparation of a measurement sample is performed, degradation of the reagent contained in the reagent container 21 could be advanced in accordance with the number of times of opening/closing of the cap portion 261. In contrast, according to Embodiment 1, when a second quality control described later is set, for example, the quality control measurement is performed in accordance with the number of times of specimen measurement, and thus, degradation of the reagent can be quickly understood.

With reference back to FIG. 2, when a reagent has been discharged into a reaction chamber 12 and a measurement sample has been prepared, the transfer unit 280 sets the reaction chamber 12 into a holding hole 291 of the detection unit 290. At this time, the two reagent dispensing units 270 are selectively used so as to realize smooth measurement.

The measurement principle of the detection unit 290 is based on a coagulation method, a synthetic substrate method, immunonephelometry, an agglutination method, or the like, for example. The detection unit 290 includes a plurality of holding holes 291. The detection unit 290 applies light to the reaction chamber 12 set in a holding hole 291, receives light having passed through the measurement sample or scattered light generated from the measurement sample, and outputs a signal corresponding to the received light intensity.

Figure 3B:
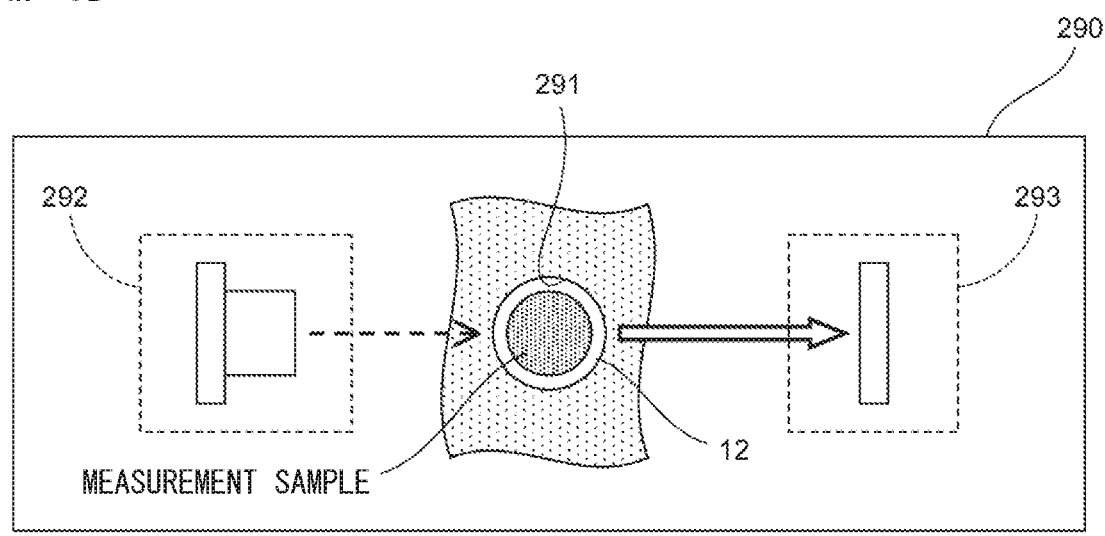
FIG. 3B is a schematic diagram showing a configuration of a detection unit according to Embodiment 1.

FIG. 3B is a schematic diagram showing a configuration of the detection unit 290.

The detection unit 290, which performs measurement related to a blood coagulation test, includes a light source part 292 and a light receiver 293. FIG. 3B shows the periphery of one holding hole 291.

The light source part 292 includes a semiconductor laser light source, and emits lights having different wavelengths.

The light source part 292 applies light to a reaction chamber 12 set in each holding hole 291. When light is applied to the measurement sample in the reaction chamber 12, light having passed through the measurement sample or light scattered by the measurement sample enters the light receiver 293. The light receiver 293 is configured as a photodetector provided for each holding hole 291. Specifically, the light receiver 293 is configured as a photoelectric tube, a photodiode, or the like. The light receiver 293 receives transmitted light or scattered light, and outputs an electric signal in accordance with the received light amount. A controller 321 of the measurement section 32 shown in FIG. 4 generates a measurement result to be used in analysis related to a blood coagulation test, on the basis of the electric signal outputted from the light receiver 293.

The measurement section 32 may perform measurement related to a biochemical test. The measurement section 32 in this case performs measurement related to a biochemical test, and includes configurations similar to those in the case of performing measurement related to a blood coagulation test. That is, the measurement section 32 in this case also applies light to the measurement sample by means of the light source part 292, and receives, by means of the light receiver 293, transmitted light or scattered light that has been generated from the measurement sample. Then, on the basis of electric signals outputted from the light receiver 293, the controller 321 generates a measurement result to be used in analysis related to a biochemical test.

Figure 4:
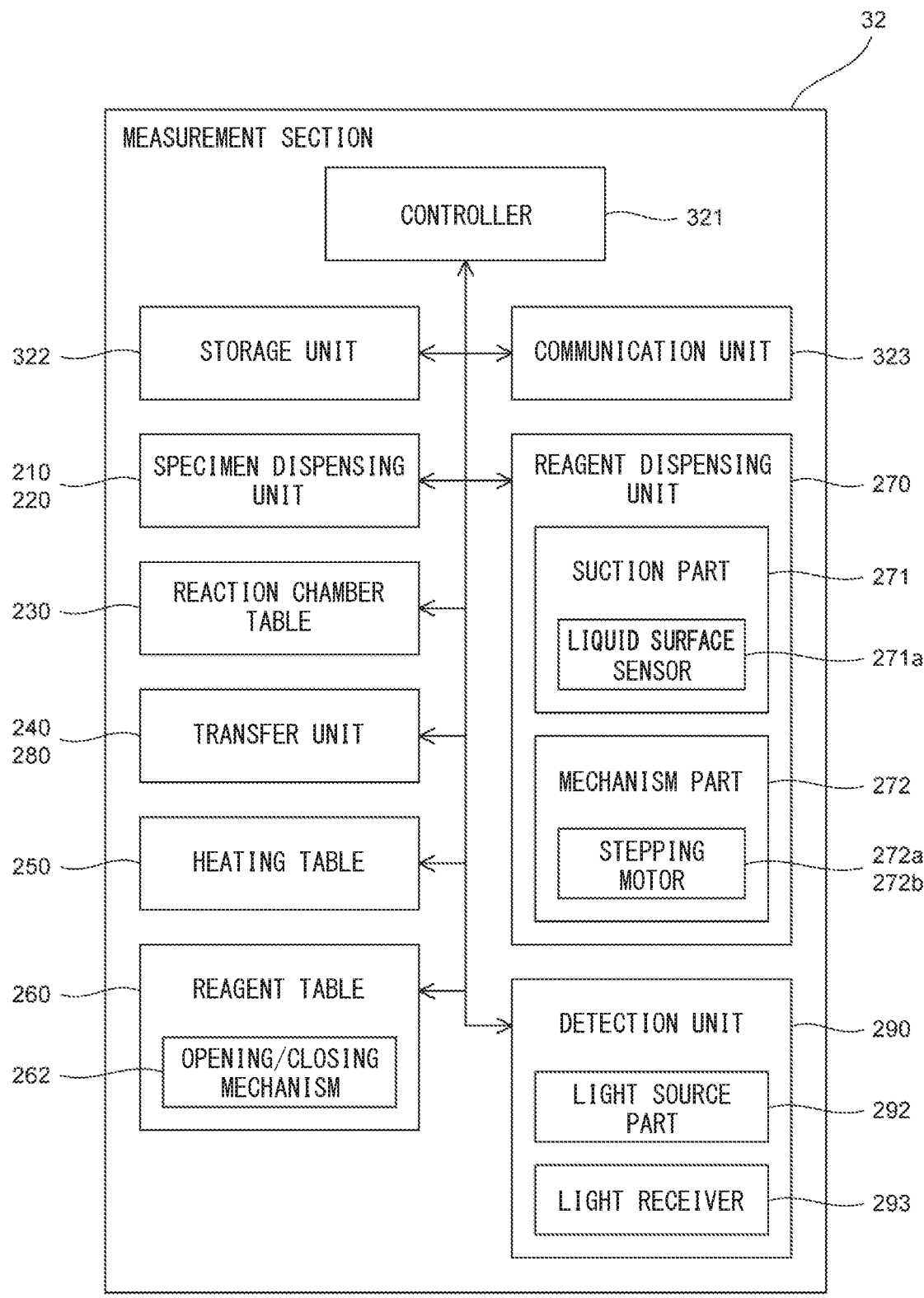
FIG. 4 is a block diagram showing a configuration of the measurement section according to Embodiment 1.

FIG. 4 is a block diagram showing a configuration of the measurement section 32.

The measurement section 32 includes the controller 321, a storage unit 322, a communication unit 323, and various types of mechanism components shown in FIG. 2 to FIG. 3B.

The controller 321 is a CPU, for example. The storage unit 322 is a ROM, a RAM, or a hard disk, for example. The controller 321 performs communication with the transport section 31 and the analysis section 33 via the communication unit 323. The communication unit 323 is an interface board for communication, for example. The controller 321 controls various components of the measurement section 32 and the transport section 31, in accordance with programs and data stored in the storage unit 322. The controller 321 causes specimen measurements and quality control measurements related to a blood coagulation test to be performed. The controller 321 stores, as a measurement result, signals outputted from the detection unit 290 into the storage unit 322, and transmits the measurement result to the analysis section 33.

Figure 5:
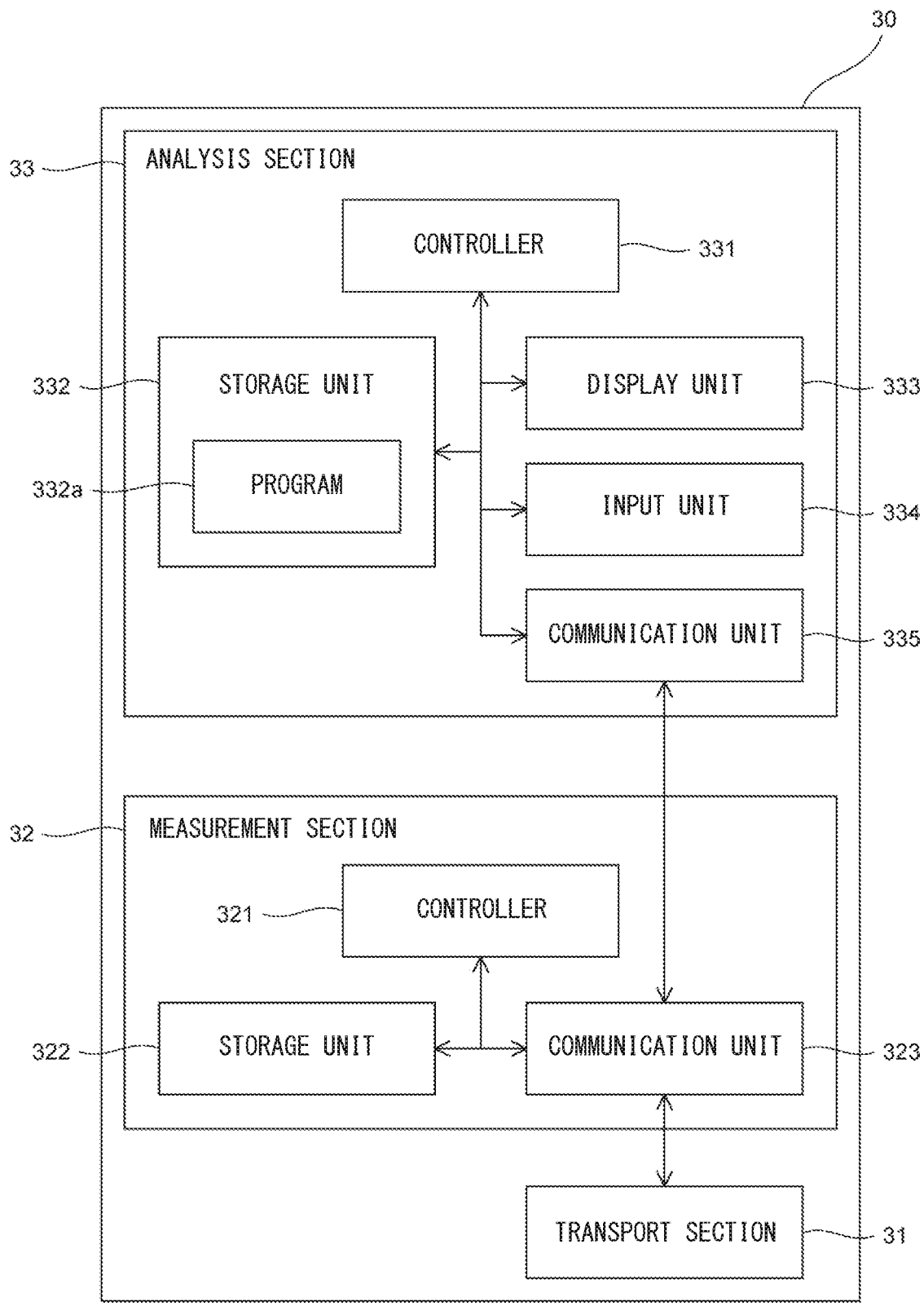
FIG. 5 is a block diagram showing a configuration of the specimen analyzer according to Embodiment 1.

FIG. 5 is a block diagram showing a configuration of the specimen analyzer 30. The specimen analyzer 30 includes the transport section 31, the measurement section 32, and the analysis section 33. In FIG. 5, configurations of the measurement section 32 other than the controller 321, the storage unit 322, and the communication unit 323 are not shown for convenience.

The analysis section 33 is configured as a personal computer, for example. The analysis section 33 includes the controller 331, a storage unit 332, a display unit 333, an input unit 334, and a communication unit 335. The controller 331 is a CPU, for example. The storage unit 332 is a ROM, a RAM, or a hard disk, for example. The storage unit 332 has stored therein a program 332a for causing the analysis section 33 to perform a predetermined process. The controller 331 performs communication with the measurement section 32 via the communication unit 335. The communication unit 335 is an interface board for communication, for example. The controller 331 controls components of the analysis section 33 and the measurement section 32 in accordance with the program 332a and data stored in the storage unit 332.

The display unit 333 is a liquid crystal display, for example. The input unit 334 is used when the operator inputs an instruction. The input unit 334 is a mouse and a keyboard, for example. The display unit 333 and the input unit 334 may be integrally configured as a touch panel-type display, or the like.

The controller 331 performs analysis related to a blood coagulation test on a specimen on the basis of a measurement result of a specimen measurement received from the measurement section 32. Specifically, the controller 331 performs analysis with respect to a measurement item such as PT, APTT, Fbg, extrinsic coagulation factor, intrinsic coagulation factor, coagulation factor XIII, HpT, TTO, FDP, D-dimer, PIC, FM, ATIII, Plg, APL, PC, VWF:Ag, VWF:RCo, ADP, collagen, epinephrine, or the like.

The types of reagents to be used for these measurement items are determined in advance. Reagent containers 21 respectively containing the reagents to be used for these measurement items are set in the reagent table 260. In order to enable measurement to be continued without being suspended even if there is no reagent remaining in a reagent container 21, unused reagent containers 21 containing the same type of reagent in advance are also set in the reagent table 260.

The controller 331 performs analysis regarding a quality control on the basis of a measurement result of a quality control measurement received from the measurement section 32. Specifically, the controller 331 transmits an instruction of a quality control measurement to the measurement section 32. The controller 321 of the measurement section 32 causes a quality control substance to be mixed with a reagent corresponding to a measurement item, to prepare a measurement sample, causes the prepared measurement sample to be measured, and transmits a measurement result to the analysis section 33. The controller 331 performs analysis with respect to the measurement item on the basis of the measurement result, and determines whether or not an analysis value is in a desired range. When the analysis value is not in the desired range, the controller 331 determines that the quality of the reagent used in the measurement for the measurement item has been decreased, and stops the measurement for this measurement item.

In Embodiment 1, the measurement section 32 and the analysis section 33 are provided as separate sections. However, the measurement section 32 and the analysis section 33 may be configured by a single apparatus. The single apparatus in this case may include the controller 321 and the controller 331 separately. Alternatively, the controller 331 may perform all the processes that are otherwise performed by the controller 321, and the controller 321 may be omitted.

A quality control group according to Embodiment 1 is described with reference to FIG. 6A to FIG. 7C.

The quality control group of Embodiment 1 includes first to fourth quality controls. The first to fourth quality controls are quality controls in which quality control measurements are respectively performed at timings based on first to fourth rules which are different from one another. The first quality control is a quality control in which a quality control measurement is performed at a predetermined time. The second quality control is a quality control in which a quality control measurement is performed every time specimen measurements are performed a predetermined number of times of measurement. The third quality control is a quality control in which a quality control measurement is performed every predetermined time interval. The fourth quality control is a quality control in which, when the remaining amount of a reagent of a first reagent container has become smaller than a predetermined amount, a quality control measurement is performed on the basis of a reagent of a second reagent container containing the same type of reagent. Hereinafter, the first quality control is referred to as "time QC", the second quality control is referred to as "test number QC", the third quality control is referred to as "time interval QC", and the fourth quality control is referred to as "the vial QC".

In Embodiment 1, the operator inputs information regarding a quality control for each measurement item, via the input unit 334 of the analysis section 33. The controller 331 of the analysis section 33 sets a quality control for each measurement item on the basis of the received information. In the description below, a case where a quality control for a predetermined measurement item is performed is described.

FIG. 6A is a schematic diagram for describing quality control measurements performed in the time QC.

Upon the current time reaching a time having been determined at the time of setting of the time QC, the controller 331 causes a quality control measurement to be performed with respect to the current reagent. Here, the current reagent is not a reagent contained in an unused reagent container 21, but is a reagent contained in a reagent container 21 currently used. In the example shown in FIG. 6A, times T1, T2, T3 have been determined at the time of setting the time QC, and a quality control measurement is performed at times T1, T2, and T3. If the quality control measurement is performed at predetermined times in this manner, in a case where the stability of the reagent is high, for example, unnecessary quality control measurements can be inhibited from being performed.

FIG. 6B is a schematic diagram for describing quality control measurements performed in the time interval QC.

The controller 331 starts counting an elapsed time in the time interval QC, and every time the elapsed time reaches a predetermined time interval, the controller 331 causes a quality control measurement to be performed with respect to the current reagent. In the example shown in FIG. 6B, a ΔT is set as a time interval at the time of setting of the time interval QC. Every time the counting of the elapsed time reaches the ΔT, a quality control measurement is performed with respect to the current reagent. If a quality control measurement is performed every predetermined time interval in this manner, in a case where the execution frequency of specimen measurements is low, for example, unnecessary quality control measurements can be inhibited from being performed.

FIG. 6C is a schematic diagram for describing quality control measurements performed in the test number QC.

The controller 331 starts counting the number of times specimen measurement occurs for a target measurement item, i.e., test number, and every time the test number reaches a predetermined number of times Nt, the controller 331 causes a quality control measurement to be performed for the current reagent. In the example shown in FIG. 6C, 3 is set as the test number Nt at the time of setting of the test number QC. Every time the count of the number of specimen measurements for the target measurement item, i.e., the test number, reaches Nt, a quality control measurement is performed for the current reagent. Thus, if a quality control measurement is performed every time specimen measurements are performed a predetermined number of times of measurement, in a case where the execution frequency of specimen measurements is high, for example, the quality control measurement can be assuredly performed.

FIGS. 7A to 7C are each a schematic diagram for describing quality control measurements performed in the vial QC.

As shown in FIG. 7A, the controller 331 estimates the number of times of specimen measurement executable in a time period Tc required for a quality control measurement. Specifically, the controller 331 estimates the number of times of executable specimen measurement, on the basis of history information regarding past execution history of specimen measurements performed by the measurement section 32. The history information is stored in the storage unit 332. When an estimated number of times Nc is estimated on the basis of history information in this manner, the estimated number of times Nc can be accurately estimated. In the example shown in FIG. 7A, 3 is estimated as the estimated number of times Nc of specimen measurement executable in the time period Tc required for the quality control measurement.

Subsequently, the controller 331 determines whether or not the remaining amount of the current reagent has become smaller than a reagent amount that is necessary for specimen measurements to be performed the estimated number of times Nc. When the remaining amount of the current reagent has become smaller than the reagent amount that is necessary for specimen measurements to be performed the estimated number of times Nc, the controller 331 causes a quality control measurement to be performed on the basis of the reagent of a reagent container 21 that contains a new reagent. Here, the new reagent is a reagent, of the same type as the current reagent, that is contained in an unused reagent container 21. For example, at the current time point in FIG. 7A, when it has been determined that the remaining amount of the current reagent is smaller than the reagent amount necessary for specimen measurements to be performed the estimated number of times Nc, a quality control measurement based on the new reagent is started.

When the quality control measurement based on the new reagent has ended, the controller 331 performs analysis regarding the quality control with respect to the new reagent. Upon determining that the new reagent is normal in the analysis regarding the quality control, the controller 331 causes a subsequent specimen measurement to be performed with use of the new reagent. Meanwhile, when having determined that the new reagent is abnormal in the analysis regarding the quality control, the controller 331 stops the specimen measurement based on the new reagent.

As shown in FIG. 7B, if it is assumed that specimen measurements have actually been performed the number of times Nc in the time period Tc required for the quality control measurement, there is no remaining amount of the current reagent, and the quality control measurement for the new reagent has ended, and thus, a specimen measurement based on the new reagent can be started. Therefore, as shown in FIG. 7C, if there is a subsequent specimen, a specimen measurement can be immediately performed.

Thus, if a quality control based on a new reagent is started when the remaining amount of the current reagent has become smaller than the reagent amount necessary for specimen measurements to be performed the estimated number of times, a specimen measurement based on a new reagent can be quickly started, and the waiting time from the end of the quality control based on the new reagent to the start of use of the new reagent can be shortened.

In the vial QC, when calculating an estimated number of times Nc of specimen measurement executable in the time period Tc required for the quality control measurement, the controller 331 may take into consideration the number of times of specimen measurement scheduled to be performed with use of the current reagent. When calculating a reagent amount to be used in specimen measurements executable in the time period Tc required for the quality control measurement, the controller 331 may take into consideration the reagent amount of the current reagent the use of which has been booked.

FIGS. 8A to 8C are each a schematic diagram for describing the vial QC according to a comparative example.

As shown in FIG. 8A, in the comparative example, when the number of times of specimen measurement that can be performed using the remaining reagent of the current reagent, i.e., the remaining test number, becomes not greater than a predetermined number of times, a quality control measurement is started. In the example shown in FIGS. 8A to 8C, the predetermined number of times is 3. As shown in FIG. 8A, since the remaining test number has reached 3 at the current time point, a quality control measurement based on a new reagent is started.

As shown in FIG. 8B, in a case where specimen measurements are performed at a high frequency after a quality control has been started, the target three specimen measurements are started before the quality control regarding the new reagent ends. In this case, specimen measurements based on the new reagent cannot be performed unless the result of the quality control based on the new reagent is determined. This causes a waiting time from the start of a specimen measurement using the current reagent until the start of a specimen measurement using the new reagent.

Meanwhile, as shown in FIG. 8C, in a case where specimen measurements are performed at a low frequency after a quality control has been started, an amount of the current reagent that allows specimen measurements to be performed still remains in the reagent container 21 after the quality control regarding a new reagent has ended. Therefore, the end of specimen measurements using the current reagent is delayed. In this case, a waiting time is caused from the end of the quality control measurement on the new reagent until the start of a specimen measurement using the new reagent. If the start of a specimen measurement based on the new reagent is delayed in this manner, the quality control result based on the quality control regarding the new reagent will not necessarily reflect the accuracy of the specimen measurement using the new reagent.

In contrast, according to Embodiment 1, the number of times of specimen measurement executable in the time period Tc required for a quality control measurement is estimated. Then, when the remaining amount of the current reagent has become smaller than the reagent amount necessary for specimen measurements to be performed the estimated number of times, a quality control measurement based on a new reagent of the same type is performed. Then, as shown in FIG. 7B, specimen measurements in the time period Tc using the current reagent can be performed while a quality control measurement using the new reagent is being performed. Thus, it is possible to easily avoid a situation where execution of a specimen measurement using the new reagent is caused to wait until the end of a quality control measurement as shown in the comparative example in FIG. 8B. Therefore, according to Embodiment 1, after a specimen measurement using the current reagent, a specimen measurement using a new reagent can be quickly started. In addition, it is possible to easily avoid a situation where, after a quality control measurement has ended, execution of a specimen measurement using a new reagent is caused to wait until there is no remaining current reagent as in the comparative example shown in FIG. 8C. Therefore, according to Embodiment 1, the quality of a new reagent can be ensured on the basis of the result of the quality control regarding the new reagent.

FIG. 9A is a conceptual diagram showing the elapsed time in the time interval QC and the test number in the test number QC stored in the storage unit 332.

The storage unit 332 of the analysis section 33 stores, for each measurement item, the elapsed time in the time interval QC and the test number in the test number QC. When a quality control measurement based on the time interval QC is performed, the controller 331 resets the elapsed time stored in the storage unit 332, starts counting an elapsed time, and updates the elapsed time stored in the storage unit 332. When a quality control measurement based on the test number QC is performed, the controller 331 resets the test number stored in the storage unit 332, increments the test number by 1 every time a specimen measurement is performed, and updates the test number stored in the storage unit 332.

In a case where the time interval QC is performed, the controller 331 causes a quality control measurement to be performed every time the elapsed time reaches the time interval $\Delta T$ shown in FIG. 6B. Accordingly, a quality control is performed every time interval $\Delta T$ in the time interval QC. In a case where the test number QC is performed, the controller 331 causes a quality control measurement to be performed every time the test number reaches the test number Nt shown in FIG. 6C. Accordingly, a quality control measurement is performed every test number Nt in the test number QC.

FIG. 9B is a conceptual diagram showing history information stored in the storage unit 332. FIG. 9C is a conceptual diagram showing the number of times of specimen measurement in each time frame of each day of week generated on the basis of history information.

As shown in FIG. 9B, for each specimen, the storage unit 332 of the analysis section 33 stores history information that includes specimen number, measurement start date, measurement start time, measurement end time, and measurement item. The history information includes information of specimens of the past 50 weeks, for example. The history information is information regarding past execution history of specimen measurements performed by the measurement section 32.

As described above, in the vial QC, the controller 331 estimates the number of times Nc of specimen measurement executable in the time period Tc, on the basis of history information regarding past execution history of specimen measurements performed by the measurement section 32. At this time, from the history information as shown in FIG. 9B, the controller 331 calculates, for each measurement item, an average of the number of times of specimen measurement in each time frame of each day of week as shown in FIG. 9C, for example. Then, on the basis of the tabulated result as shown in FIG. 9C, the controller 331 estimates the number of times of specimen measurement executable in the time period Tc required for a quality control measurement. Specifically, with reference to FIG. 9C, the controller 331 calculates an average Na of the number of times of specimen measurement in a time frame to which the current time belongs, and obtains the calculated average number of times Na, as an estimated number of times Nc of specimen measurement predicted to be performed in the time period Tc. Then, the controller 331 calculates a predicted use amount necessary for specimen measurements to be performed the estimated number of times Nc, and when the remaining amount of the current reagent has become smaller than the predicted use amount, the controller 331 causes a quality control measurement to be performed.

When the number of times of specimen measurement predicted to be performed in a day of week and a time frame to which the current time belongs is obtained on the basis of history information in this manner, the reagent amount necessary for specimen measurements to be performed in a time period required for a quality control measurement can be appropriately estimated.

In Embodiment 1, as shown in FIG. 9C, the controller 331 calculates only the average Na of the number of times of specimen measurement in a day of week and a time frame to which the current time belongs, instead of calculating all the averages of the respective days of week and the respective time frames.

Next, with reference to FIGS. 10 to 13, screens to be used when setting a quality control are described. At the time of installing the specimen analyzer 30, reviewing operation of quality controls, or the like, the operator causes the screens shown in FIGS. 10 to 13 to be displayed on the display unit 333, and performs setting of a quality control.

Figure 10:
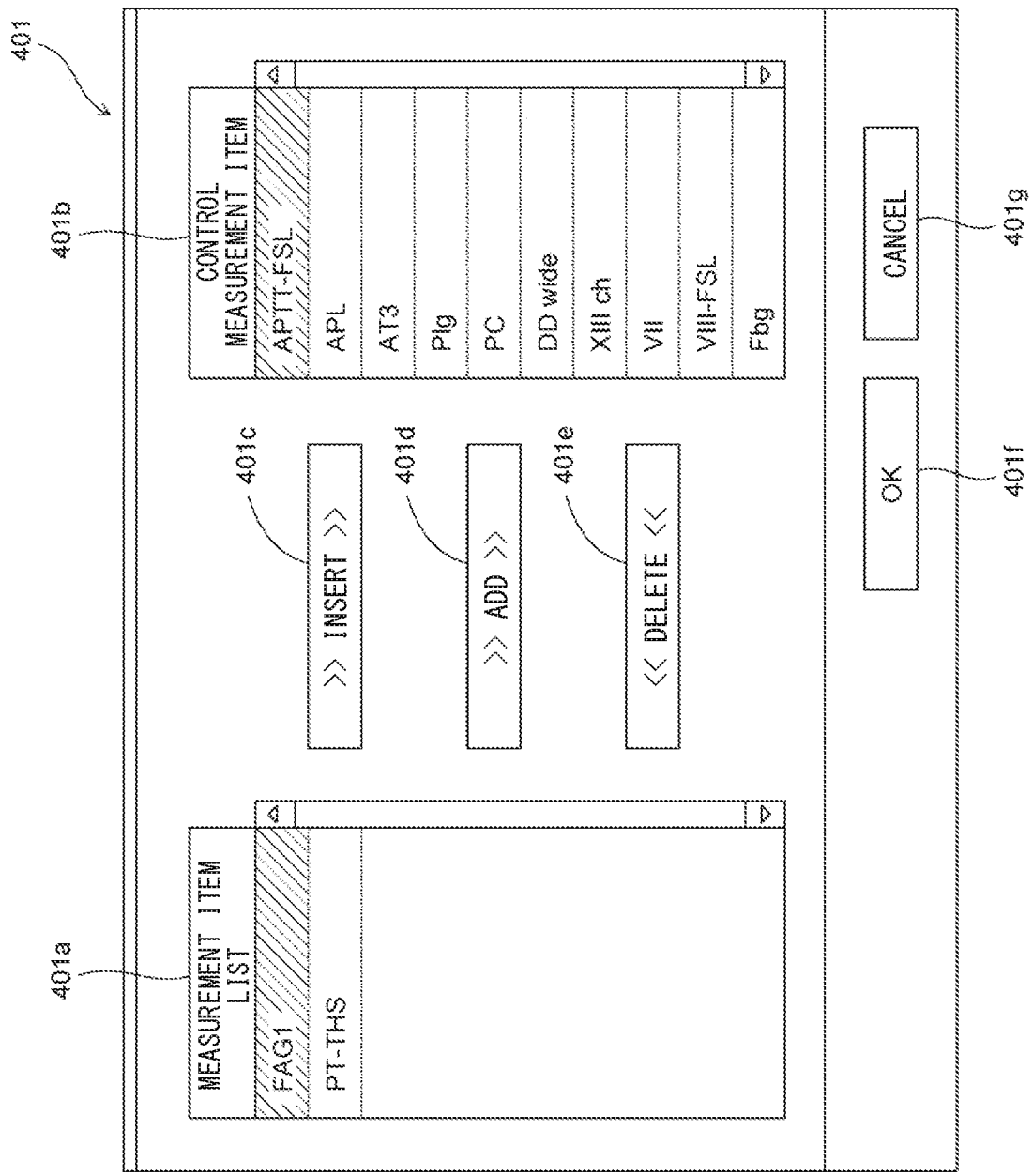
FIG. 10 is a schematic diagram showing a configuration of a control measurement item selection screen displayed on a display unit according to Embodiment 1.

As shown in FIG. 10, a control measurement item selection screen 401 includes a measurement item list 401a, a control measurement item list 401b, an insertion button 401c, an addition button 401d, a deletion button 401e, an OK button 401f, and a cancelation button 401g. The operator operates the input unit 334 to display the control measurement item selection screen 401.

The measurement item list 401a is a list of measurement items that are not set as control targets among all measurement items. The control measurement item list 401b is a list of measurement items set as control targets. When the insertion button 401c is operated, the controller 331 inserts a measurement item selected in the measurement item list 401a, below a measurement item selected in the control measurement item list 401b. When the addition button 401d is operated, the controller 331 adds a measurement item selected in the measurement item list 401a, at the bottom of the control measurement item list 401b. When the deletion button 401e is operated, the controller 331 deletes a measurement item selected in the control measurement item list 401b, and adds the deleted measurement item to the measurement item list 401a.

When the OK button 401f is operated, the controller 331 stores the measurement items in the control measurement item list 401b into the storage unit 332, and closes the control measurement item selection screen 401. When the cancelation button 401g is operated, the controller 331 discards the information set in the control measurement item list 401b and closes the control measurement item selection screen 401.

As shown in FIG. 11, an edit measurement item selection screen 402 includes a measurement item list 402a and an item edit button 402b. The operator operates the input unit 334 to display the edit measurement item selection screen 402.

The measurement item list 402a displays a list of measurement items as control targets that are previously set through the control measurement item selection screen 401 in FIG. 10 and that are stored in the storage unit 332. In the measurement item list 402a, for each measurement item, a part of settings for quality control is displayed. When the item edit button 402b is operated, the controller 331 reads setting information of the quality controls for a measurement item selected in the measurement item list 402a, and causes the display unit 333 to display a reception screen 410 in a state of reflecting the read setting information. The setting information of quality controls for the measurement item is stored in advance as initial values in the storage unit 332, and also stored in the storage unit 332 through the reception screens 410, 420.

Figure 12:
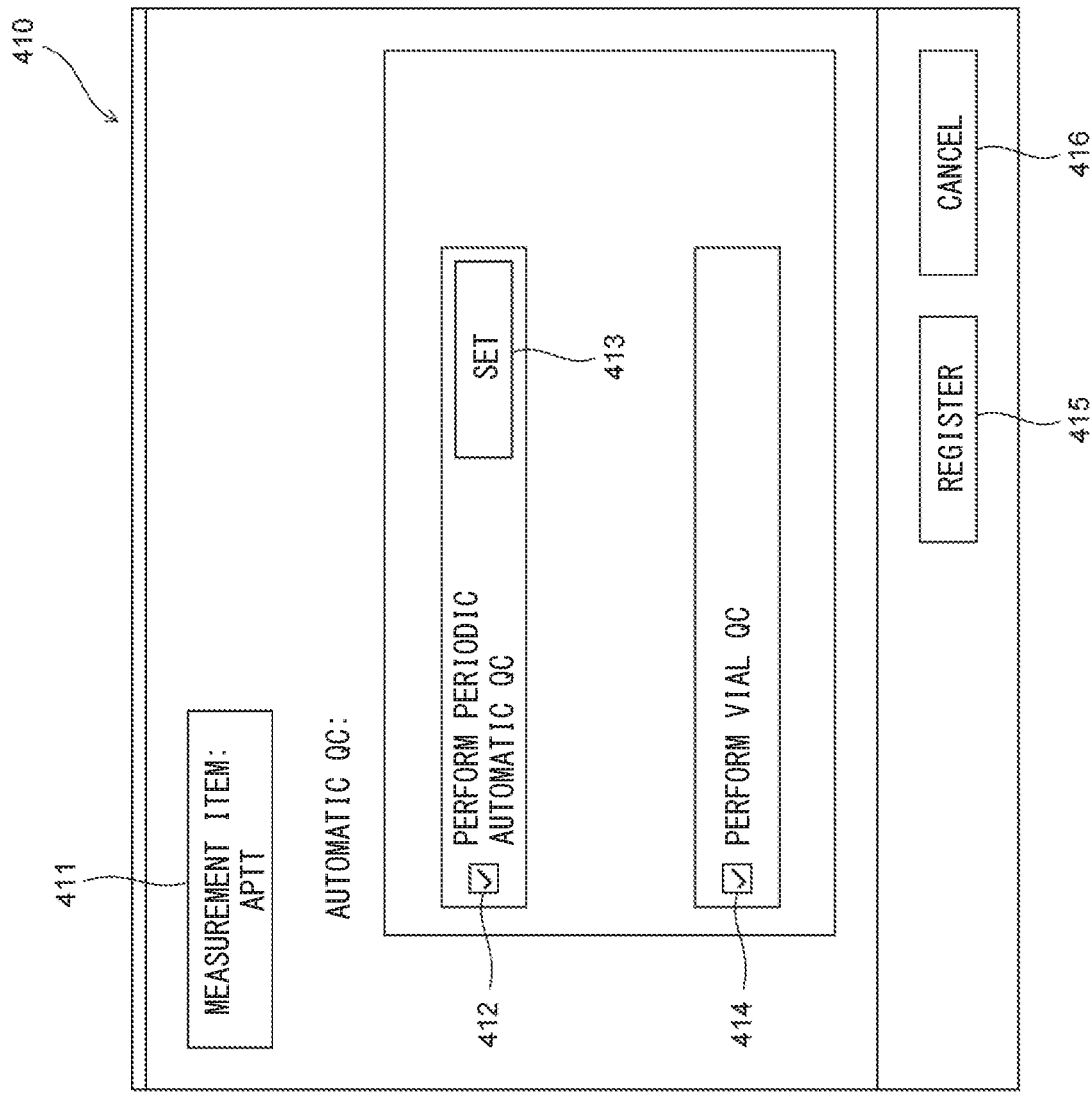
FIG. 12 is a schematic diagram showing a configuration of a reception screen displayed on the display unit according to Embodiment 1.

As shown in FIG. 12, the reception screen 410 includes a measurement item display region 411, a check box 412, a setting button 413, a check box 414, a registration button 415, and a cancelation button 416.

The measurement item display region 411 indicates a measurement item that is selected on the edit measurement item selection screen 402 and that is set on the reception screen 410. The check box 412 is an operation portion for setting whether or not to perform a periodic automatic QC. The periodic automatic QC includes the time QC, the time interval QC, and the test number QC. By operating the check box 412, the operator can set whether or not to perform, in a batch, the periodic automatic QC set on the reception screen 420 described later. The setting button 413 is a button for more specifically setting the periodic automatic QC. When the setting button 413 is operated, the controller 331 causes the display unit 333 to display the reception screen 420 described later. The check box 414 is an operation portion for setting whether or not to perform the vial QC.

When the registration button 415 is operated, the controller 331 stores, into the storage unit 332, the setting information set on the reception screen 410 and the reception screen 420 described later, and closes the reception screen 410. When the cancelation button 416 is operated, the controller 331 discards the setting information set on the reception screens 410, 420, and closes the reception screen 410.

Figure 13:
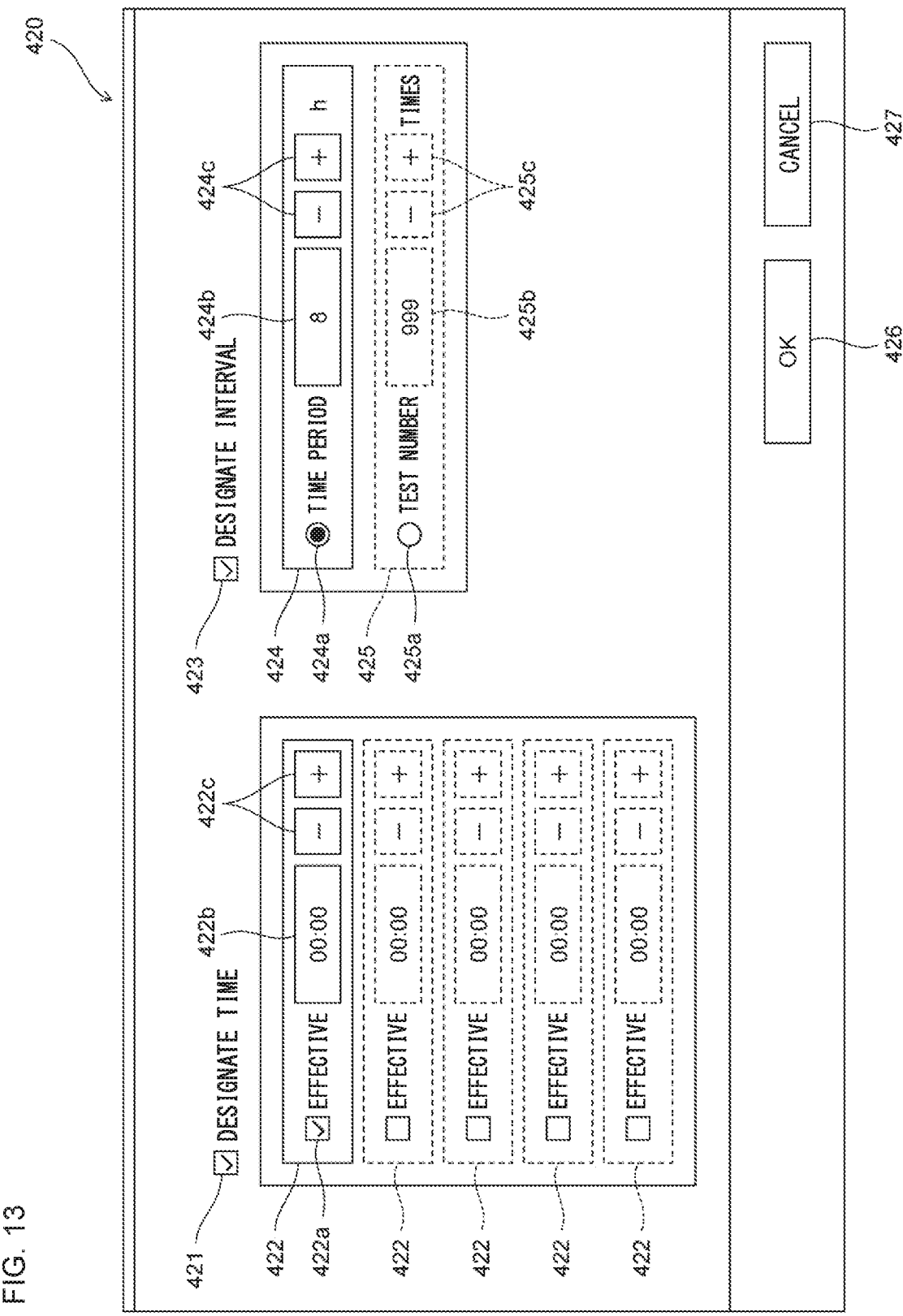
FIG. 13 is a schematic diagram showing a configuration of a reception screen displayed on the display unit according to Embodiment 1.

As shown in FIG. 13, the reception screen 420 includes a check box 421, a plurality of setting regions 422, a check box 423, and setting regions 424, 425.

The check box 421 is an operation portion for setting whether or not to perform the time QC. When the check box 421 enters a checked state, the setting of a setting region 422 that has a check box 422a in a checked state becomes effective. The setting region 422 is a region for setting the time at which a quality control is to be performed in the time QC. When a button 422c is operated, the time in a time input region 422b is changed. In a case where the check box 422a is in a checked state, when the check box 421 enters a checked state, the time in the setting region 422 becomes effective. In the example shown in FIG. 13, the time in the top setting region 422 among the five setting regions has become effective.

The check box 423 is an operation portion for setting whether to perform the time interval QC or the test number QC. When the check box 423 has entered a checked state, the setting in the setting region 424 or the setting region 425 becomes effective. The setting region 424 is a region for setting a time interval at which a quality control is performed in the time interval QC. When a button 424c is operated, the time period in a time interval input region 424b is changed. In a case where a radio button 424a is in a selected state, when the check box 423 enters a checked state, the time interval QC becomes effective. The setting region 425 is a region for setting a test number a quality control is to be performed in the test number QC. When a button 425c is operated, the test number in a test number input region 425b is changed. In a case where a radio button 425a is in a selected state, when the check box 423 enters a checked state, the test number QC becomes effective.

The radio buttons 424a and 425a operate in conjunction with each other, and when one of the radio buttons 424a and 425a enters a selected state, the other of the radio buttons 424a and 425a enters a non-selected state. Accordingly, only one of the time interval QC and the test number QC can be set as a quality control to be performed.

When an OK button 426 is operated, the controller 331 temporarily stores the setting content of the reception screen 420 into the storage unit 332 and closes the reception screen 420. When a cancelation button 427 is operated, the controller 331 discards the setting content of the reception screen 420 and closes the reception screen 420.

Figure 14:
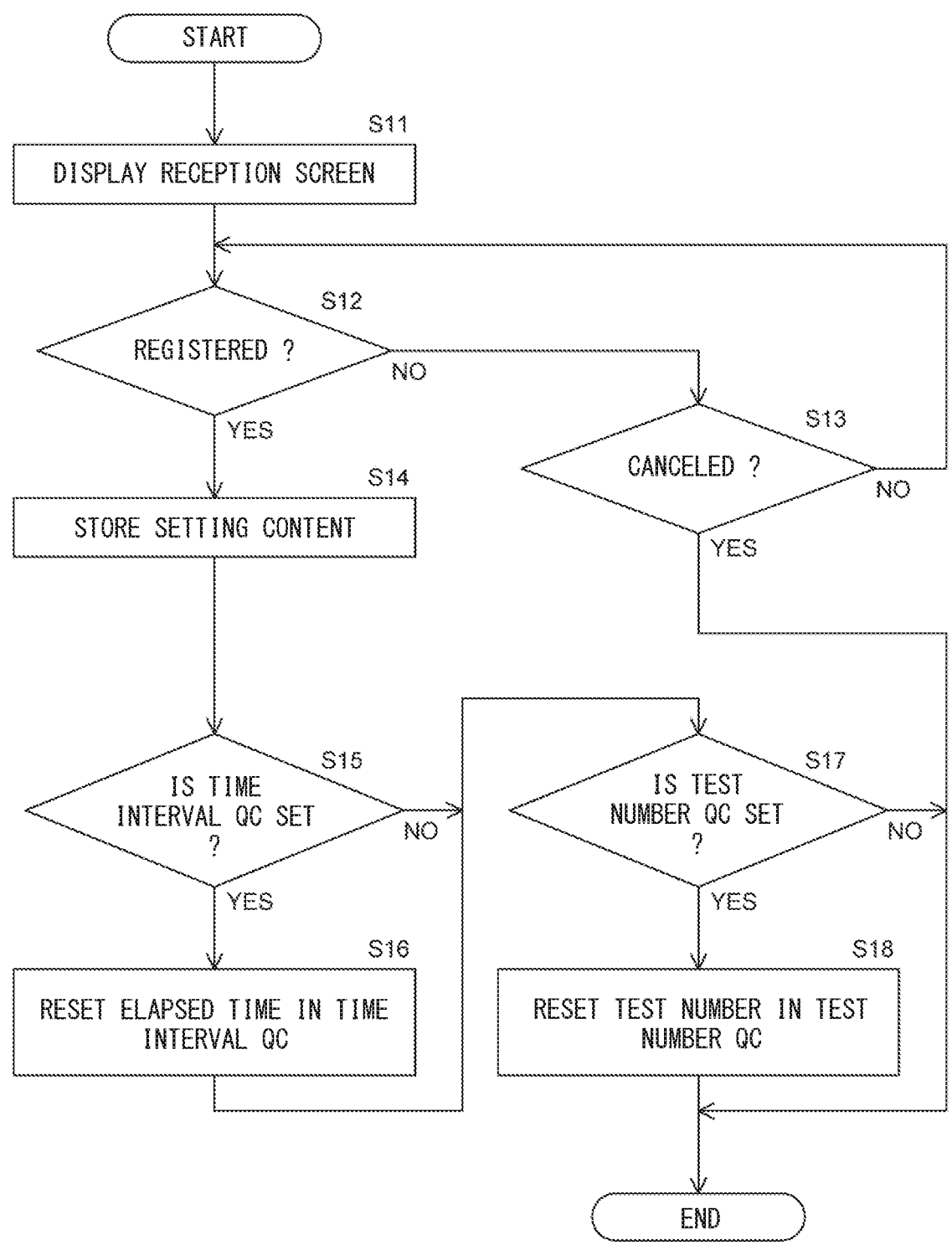
FIG. 14 is a flow chart showing a process for displaying a reception screen according to Embodiment 1.

With reference to the flow chart in FIG. 14, 15, the process of displaying the reception screen 410, 420 on the display unit 333 are described. The process shown in FIG. 14, 15 is performed for each measurement item.

When the operator selects a measurement item on the edit measurement item selection screen 402 by operating the input unit 334, and operates the item edit button 402b, the controller 331 starts the process shown in FIG. 14.

In step S11, the controller 331 reads setting information stored in the storage unit 332, and causes the display unit 333 to display the reception screen 410 in a state of reflecting the read setting information. The operator operates the reception screen 410 shown in FIG. 12 through the input unit 334, and inputs settings for quality control. In addition, the operator operates the setting button 413 on the reception screen 410 shown in FIG. 12 through the input unit 334, thereby causing the reception screen 420 shown in FIG. 13 to be displayed, and operates the reception screen 420 to input settings for quality control.

Figure 15:
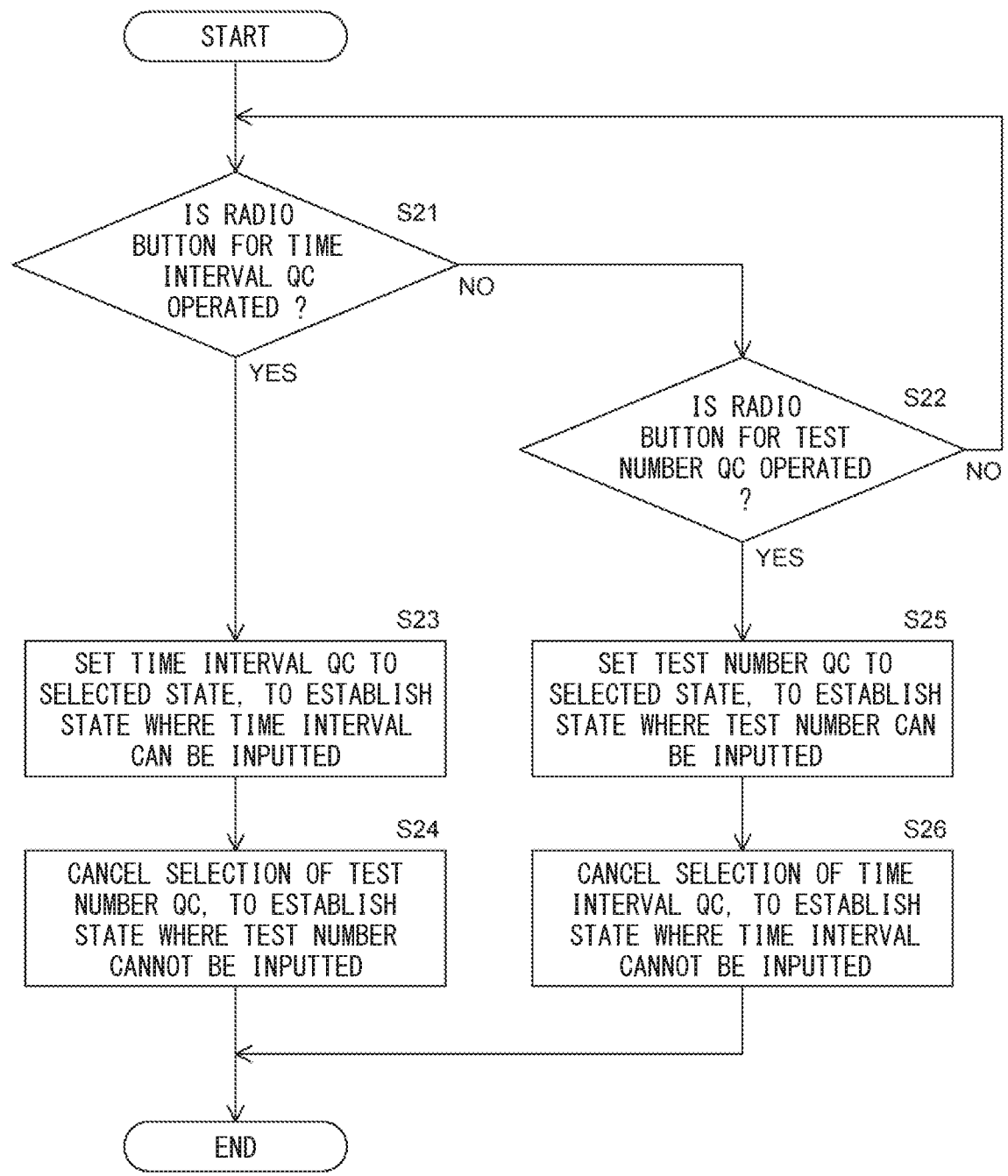
FIG. 15 is a flow chart showing a process of selecting either one of the time interval QC and the test number QC on a reception screen according to Embodiment 1.

FIG. 15 is a flow chart showing a process with respect to the operation of the radio button 424a, 425a on the reception screen 420. The controller 331 determines, in step S21, whether or not the radio button 424a for the time interval QC has been operated, and determines, in step S22, whether or not the radio button 425a for the test number QC has been operated.

When the radio button 424a for the time interval QC has been operated, the controller 331 sets, in step S23, the time interval QC to a selected state, thereby establishing a state where a time interval can be inputted. Specifically, the controller 331 sets the radio button 424a to a selected state, thereby establishing a state where the time interval input region 424b and the button 424c can be operated. In step S24, the controller 331 cancels the selected state of the test number QC, thereby establishing a state where a test number cannot be inputted. Specifically, the controller 331 sets the radio button 425a to a non-selected state, thereby establishing a state where the test number input region 425b and the button 425c cannot be operated.

Meanwhile, when the radio button 425a of the test number QC has been operated, the controller 331 sets, in step S25, the test number QC to a selected state, thereby establishing a state where a test number can be inputted. Specifically, the controller 331 sets the radio button 425a to a selected state, thereby establishing a state where the test number input region 425b and the button 425c can be operated. In step S26, the controller 331 cancels the selected state of the time interval QC, thereby establishing a state where a time interval cannot be inputted. Specifically, the controller 331 sets the radio button 424a to a non-selected state, thereby establishing a state where the time interval input region 424b and the button 424c cannot be operated.

When the process of step S24 or step S26 has ended, the controller 331 returns the process to step S21, and repeatedly performs the process shown in FIG. 15. When the OK button 426 or the cancelation button 427 on the reception screen 420 has been operated, the controller 331 ends the process shown in FIG. 15.

As described above, in Embodiment 1, since only either one of the radio buttons 424a and 425a can be selected, either one of the time interval QC and the test number QC can be alternatively set. As described with reference to FIGS. 6B and 6C, the time interval QC and the test number QC are each performed at a substantially constant interval. Therefore, if either one of them is performed, a necessary quality control can be performed. According to Embodiment 1, either one of the time interval QC and the test number QC can be alternatively set. Thus, unnecessary quality controls can be inhibited from being performed, and consumption of quality control substances and reagents can be suppressed. In addition, since setting of unnecessary quality controls can be avoided, the setting operation by the operator can be simplified.

With reference back to FIG. 14, the controller 331 determines, in step S12, whether or not the registration button 415 on the reception screen 410 has been operated. In step S13, the controller 331 determines whether or not the cancelation button 416 on the reception screen 410 has been operated. When the registration button 415 has been operated, the controller 331 advances the process to step S14. Meanwhile, when the cancelation button 416 has been operated, the controller 331 discards the setting content set through the reception screens 410, 420, and ends the process in FIG. 14.

In step S14, the controller 331 stores, into the storage unit 332, the setting content set through the reception screens 410, 420. As described above, in Embodiment 1, the controller 331 causes the display unit 333 to display the reception screens 410, 420 for receiving settings for quality controls included in the quality control group, and sets each quality control received through the reception screens 410, 420, as a quality control to be performed. Accordingly, the operator can easily set each quality control included in the quality control group through the reception screens 410, 420.

As described above, when the operator has selected a measurement item on the edit measurement item selection screen 402 and then operates the item edit button 402b, the controller 331 causes the reception screen 410 for setting a quality control to be displayed, for the measurement item received from the operator through the input unit 334. Accordingly, an appropriate quality control can be set for each measurement item.

In step S15, the controller 331 determines whether or not the time interval QC has been set. When the check box 412 is in a checked state on the reception screen 410, and the check box 423 is in a checked state and the radio button 424a is in a selected state on the reception screen 420, the controller 331 determines that the time interval QC is set. When the time interval QC is set, the controller 331 resets, in step S16, the elapsed time in the time interval QC for the measurement item. As described with reference to FIG. 9A, the elapsed time in the time interval QC is stored in the storage unit 332 for each measurement item, and is updated in real time in accordance with a lapse of time. In step S16, the elapsed time in the time interval QC for the target measurement item is set to 0.

In step S17, the controller 331 determines whether or not the test number QC is set. When the check box 412 is in a checked state on the reception screen 410, and the check box 423 is in a checked state and the radio button 425a is in a selected state on the reception screen 420, the controller 331 determines that the test number QC is set. When the test number QC is set, the controller 331 resets, in step S18, the test number in the test number QC for the measurement item. As described with reference to FIG. 9A, the test number in the test number QC is stored in the storage unit 332 for each measurement item, and is incremented in real time every time a specimen measurement is performed for a target measurement item. In step S18, the test number in the test number QC for the target measurement item is set to 0.

Figure 16A:
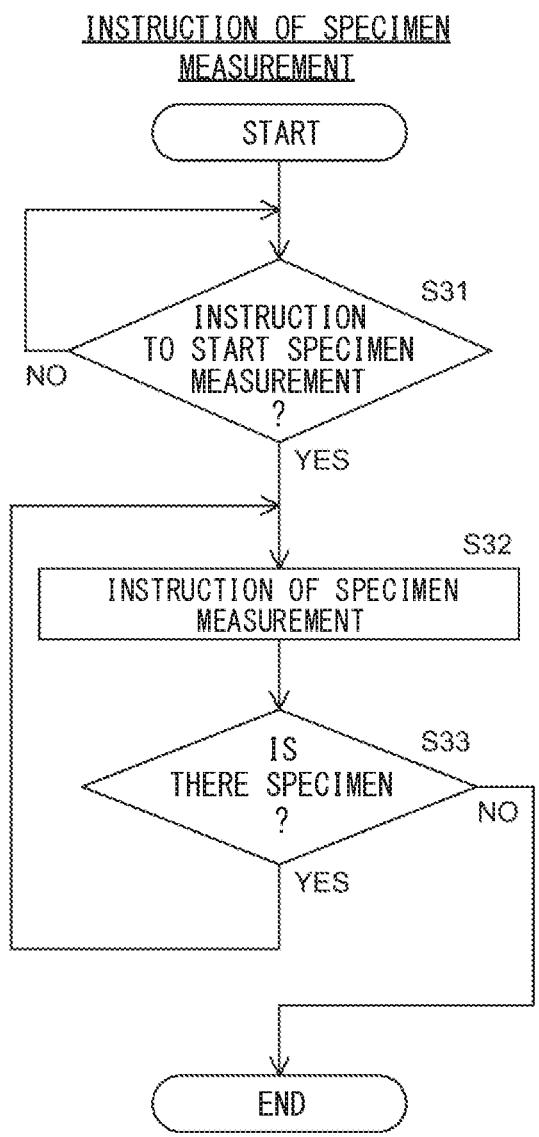
FIG. 16A is a flow chart showing a process with respect to an instruction of a specimen measurement according to Embodiment 1.

FIG. 16A is a flow chart showing a process with respect to an instruction of a specimen measurement.

In step S31, the controller 331 determines whether or not an instruction to start a specimen measurement has been received through the input unit 334 from the operator. Upon receiving an instruction to start a specimen measurement, the controller 331 transmits, in step S32, an instruction to perform a specimen measurement to the controller 321 of the measurement section 32, thereby causing the measurement section 32 to perform a specimen measurement. In step S33, on the basis of a signal from the measurement section 32, the controller 331 determines whether or not there is a subsequent specimen. When there is a subsequent specimen, the controller 331 returns the process to step S32, and transmits an instruction of a specimen measurement for the subsequent specimen. Meanwhile, when there is no subsequent specimen, the controller 331 ends the process shown in FIG. 16A. The process with respect to an instruction of a specimen measurement shown in FIG. 16A is repeatedly performed.

Figure 16B:
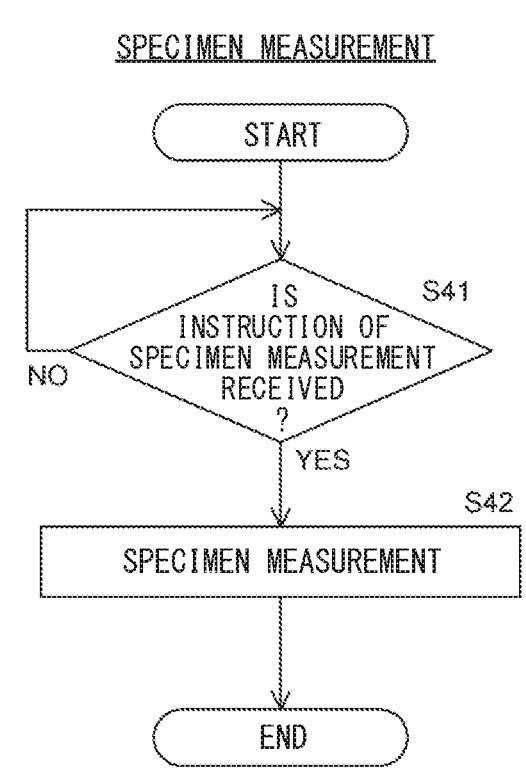
FIG. 16B is a flow chart showing a process of a specimen measurement according to Embodiment 1.

FIG. 16B is a flow chart showing a process of a specimen measurement.

In step S41, the controller 321 of the measurement section 32 determines whether or not the instruction of the specimen measurement transmitted from the analysis section 33 in step S32 in FIG. 16A has been received. Upon receiving the instruction of the specimen measurement, the controller 321 drives, in step S42, components of the measurement section 32 to perform a specimen measurement. That is, with respect to a measurement item included in the instruction of the specimen measurement, the controller 321 causes a specimen and a reagent corresponding to the measurement item to be mixed together, thereby preparing a measurement sample, and causes the prepared measurement sample to be measured. The process of a specimen measurement shown in FIG. 16B is repeatedly performed.

Figure 16C:
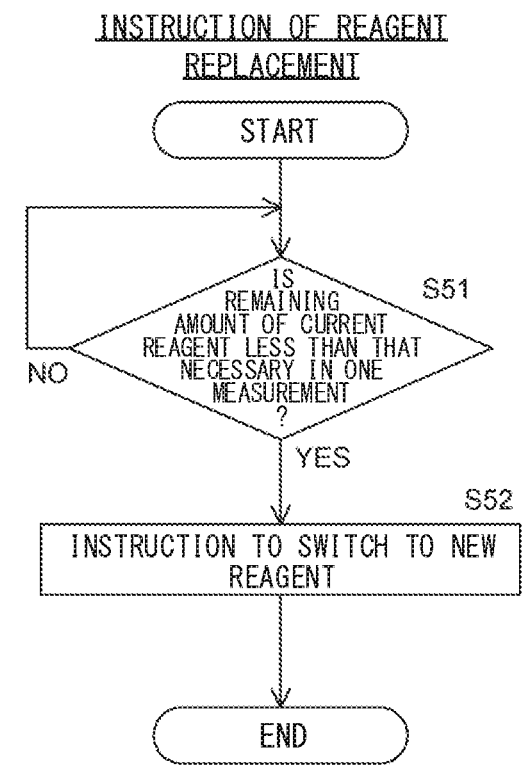
FIG. 16C is a flow chart showing a process with respect to an instruction of reagent replacement according to Embodiment 1.

FIG. 16C is a flow chart showing a process with respect to an instruction of reagent replacement.

In step S51, the controller 331 determines whether or not the remaining amount of a current reagent is less than the amount to be used in one specimen measurement for a measurement item corresponding to this reagent.

Here, as described above, the reagent dispensing unit 270 includes the liquid surface sensor 271a for detecting the liquid surface at the time of suction performed by the suction part 271, and the stepping motor 272b for moving the suction part 271 in the up-down direction. Every time suction of a reagent by the suction part 271 is performed, the controller 331 obtains the remaining amount of the reagent in the reagent container 21, on the basis of the number of pulses inputted to the stepping motor 272b and the liquid surface detection by the liquid surface sensor 271a.

That is, when the initial position of the leading end of the suction part 271 is defined as H, the number of pulses inputted to the stepping motor 272b from the time when the suction part 271 is at the initial position to the time when the liquid surface is detected is defined as P, the lowering amount of the suction part 271 when a unit pulse is inputted to the stepping motor 272b is defined as D, and the internal area of a reagent container 21 is defined as S, a remaining amount T of the reagent contained in the reagent container 21 is calculated by Formula (1) below.

$$T=(H-P\times D)\times S \quad (1)$$

When the suction part 271 is lowered for performing dispensing of a current reagent, the controller 331 obtains a remaining amount of the reagent before being suctioned, on the basis of Formula (1) above. Further, by subtracting a reagent amount to be suctioned in one dispensing, from the remaining amount of the reagent before being suctioned, the controller 331 obtains a remaining amount of the current reagent. The controller 331 stores the thus obtained remaining amount of the current reagent into the storage unit 332. In step S51, it is determined whether or not the remaining amount of the current reagent updated every dispensing of the reagent is less than the amount necessary for one measurement, at the execution time point of step S51.

When the remaining amount of the current reagent is less than the amount necessary for one measurement, the controller 331 transmits, to the controller 321 of the measurement section 32 in step S52, an instruction to switch the reagent to be dispensed, from the current reagent to a new reagent. That is, the controller 331 causes use of the reagent container 21 containing the current reagent to end, and causes a subsequent specimen measurement to be performed with use of a new reagent of the same type as the current reagent. The process with respect to an instruction of reagent replacement shown in FIG. 16C is repeatedly performed.

Next, with reference to FIG. 17A to FIG. 19, processes of the time QC, the time interval QC, the test number QC, and the vial QC are described. The processes in FIG. 17A, FIG. 18A, FIG. 18B, and FIG. 19 are repeatedly performed for each measurement item. The processes in FIG. 17A, FIG. 18A, FIG. 18B, and FIG. 19 are started upon start of a specimen measurement in FIG. 16A, and are repeated until specimen measurements end. That is, these processes are repeated from determination as YES in step S31 until determination as NO in step S33. The processes in FIG. 17A, FIG. 18A, FIG. 18B, and FIG. 19 may be started, upon setting of executions of the time QC, the time interval QC, the test number QC, and the vial QC, respectively, and may be repeated until the specimen analyzer 30 is stopped.

As shown in FIG. 17A, in step S101, the controller 331 refers to the setting information stored in the storage unit 332, and determines whether or not the current time has reached the set time for the time QC set in the time input region 422b on the reception screen 420. When the current time has reached the set time, the controller 331 transmits, in step S102, an instruction to perform a quality control measurement to the controller 321 of the measurement section 32, thereby causing the measurement section 32 to perform a quality control measurement.

FIG. 17B is a flow chart showing a process of the quality control measurement.

In step S61, the controller 321 of the measurement section 32 determines whether or not the instruction of the quality control measurement transmitted from the analysis section 33 in step S102 in FIG. 17A has been received. When having received the instruction of the quality control measurement, the controller 321 drives, in step S62, components of the measurement section 32 to perform a quality control measurement. That is, with respect to a measurement item included in the instruction of the quality control measurement, the controller 321 causes a quality control substance and a reagent corresponding to the measurement item to be mixed together, thereby preparing a measurement sample, and causes the prepared measurement sample to be measured. The process of the quality control measurement shown in FIG. 17B is repeatedly performed. Also when an instruction of a quality control measurement is transmitted in step S112 in FIG. 18A, step S122 in FIG. 18B, and step S134 in FIG. 19, the controller 321 causes a quality control measurement to be performed in accordance with the process shown in FIG. 17B.

As described above, when a quality control substance and a reagent corresponding to a measurement item are mixed together to prepare a measurement sample, and the prepared measurement sample is measured, even in a case where there are a plurality of reagents for each measurement item, a quality control measurement based on a reagent corresponding to the measurement item can be assuredly performed.

With reference back to FIG. 17A, in step S103, the controller 331 resets the elapsed time in the time interval QC and the test number in the test number QC.

The quality control measurement is performed at temporal intervals so as to ensure the accuracy of specimen measurements. Thus, the necessity of performing a plurality of quality control measurements at close timings is low. According to Embodiment 1, when a quality control measurement based on the time QC is performed in step S102, the count of the elapsed time in the time interval QC and the count of the test number in the test number QC are reset in step S103. Accordingly, it is possible to inhibit the time interval QC and the test number QC from being performed at close timings after a quality control measurement has been performed at a predetermined time. In addition, unnecessary quality controls are inhibited from being performed, and thus, consumption of quality control substances and reagents can be suppressed.

Subsequently, in step S104, the controller 331 causes the process to wait until a result of the quality control measurement performed in step S102 is obtained. Upon obtaining the result of the quality control measurement, the controller 331 performs, in step S105, analysis regarding the quality control on the basis of the result of the quality control measurement, and determines whether or not there is an abnormality in the reagent. When having determined that there is an abnormality in the reagent, the controller 331 drives, in step S106, the measurement section 32 to stop the specimen measurement started in step S31 in FIG. 16A. Meanwhile, when having determined that there is no abnormality in the reagent, step S106 is skipped and the process in FIG. 17A ends.

Figure 18A:
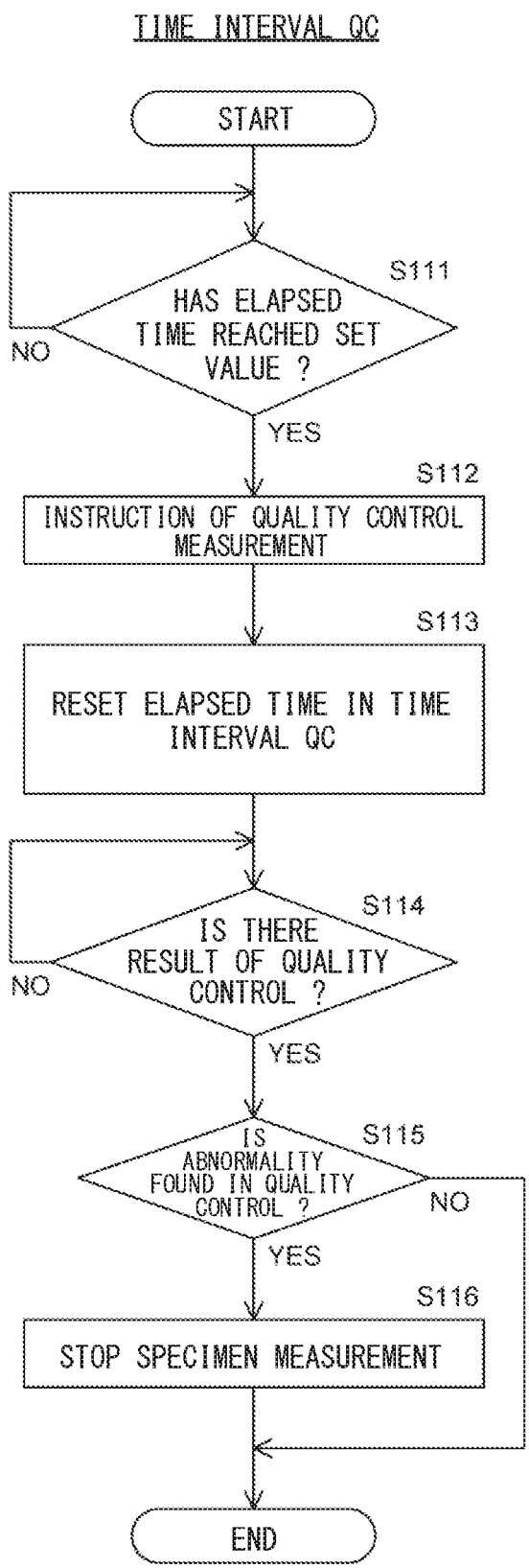
FIG. 18A is a flow chart showing a process of the time interval QC according to Embodiment 1.

As shown in FIG. 18A, in step S111, the controller 331 refers to the elapsed time stored in the storage unit 332 as shown in FIG. 9A, and determines whether or not the count of the elapsed time in the time interval QC has reached the set value. When the count of the elapsed time has reached the set value, the controller 331 transmits, in step S112, an instruction to perform a quality control measurement to the controller 321 of the measurement section 32, thereby causing the measurement section 32 to perform a quality control measurement. Then, in step S113, the controller 331 resets the elapsed time in the time interval QC.

Subsequently, in step S114, the controller 331 causes the process to wait until a result of the quality control measurement performed in step S112 is obtained. Upon obtaining the result of the quality control measurement, the controller 331 performs, in step S115, analysis regarding the quality control on the basis of the result of the quality control measurement, and determines whether or not there is an abnormality in the reagent. When having determined that there is an abnormality in the reagent, the controller 331 drives, in step S116, the measurement section 32 to stop the specimen measurement started in step S31 in FIG. 16A. Meanwhile, when having determined that there is no abnormality in the reagent, step S116 is skipped and the process in FIG. 18A ends.

Figure 18B:
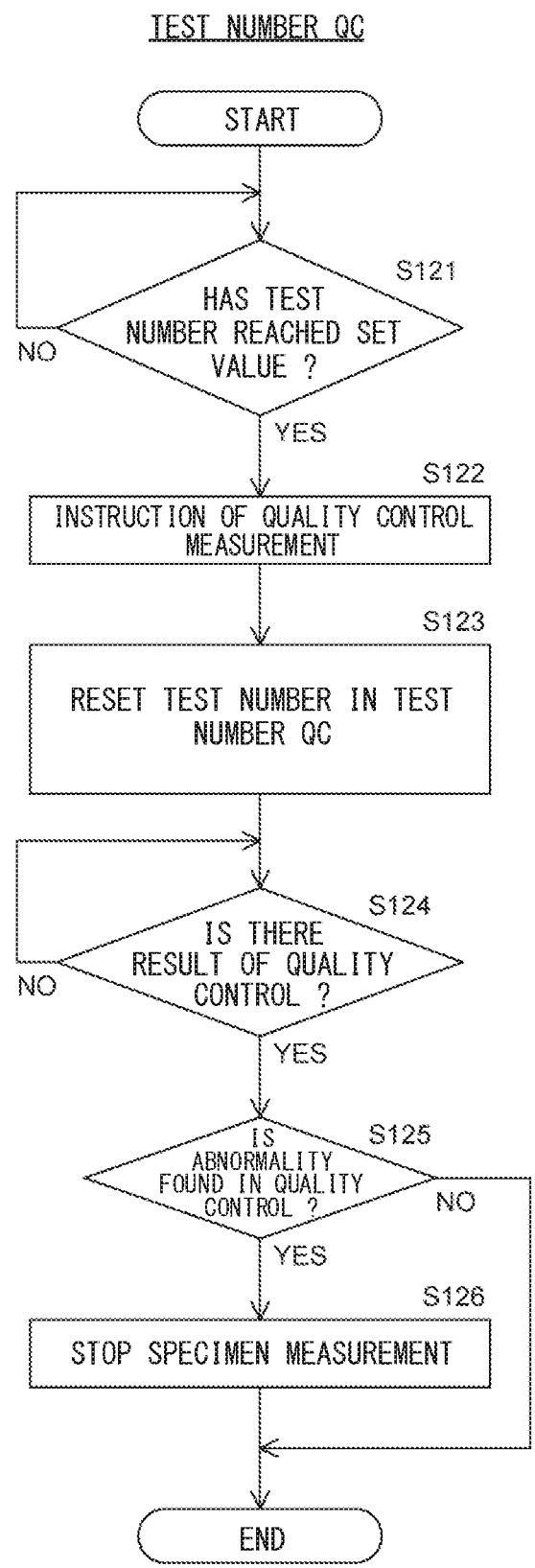
FIG. 18B is a flow chart showing a process of the test number QC according to Embodiment 1.

As shown in FIG. 18B, in step S121, the controller 331 refers to the test number stored in the storage unit 332 as shown in FIG. 9A, and determines whether or not the count of the test number in the test number QC has reached the set value. When the count of the test number has reached the set value, the controller 331 transmits, in step S122, an instruction to perform a quality control measurement to the controller 321 of the measurement section 32, thereby causing the measurement section 32 to perform a quality control measurement. Then, in step S123, the controller 331 resets the test number in the test number QC.

Subsequently, in step S124, the controller 331 causes the process to wait until a result of the quality control measurement performed in step S122 is obtained. Upon obtaining the result of the quality control measurement, the controller 331 performs, in step S125, analysis regarding the quality control on the basis of the result of the quality control measurement, and determines whether or not there is an abnormality in the reagent. When having determined that there is an abnormality in the reagent, the controller 331 drives, in step S126, the measurement section 32 to stop the specimen measurement started in step S31 in FIG. 16A. Meanwhile, when having determined that there is no abnormality in the reagent, step S126 is skipped and the process in FIG. 18B ends.

Figure 19:
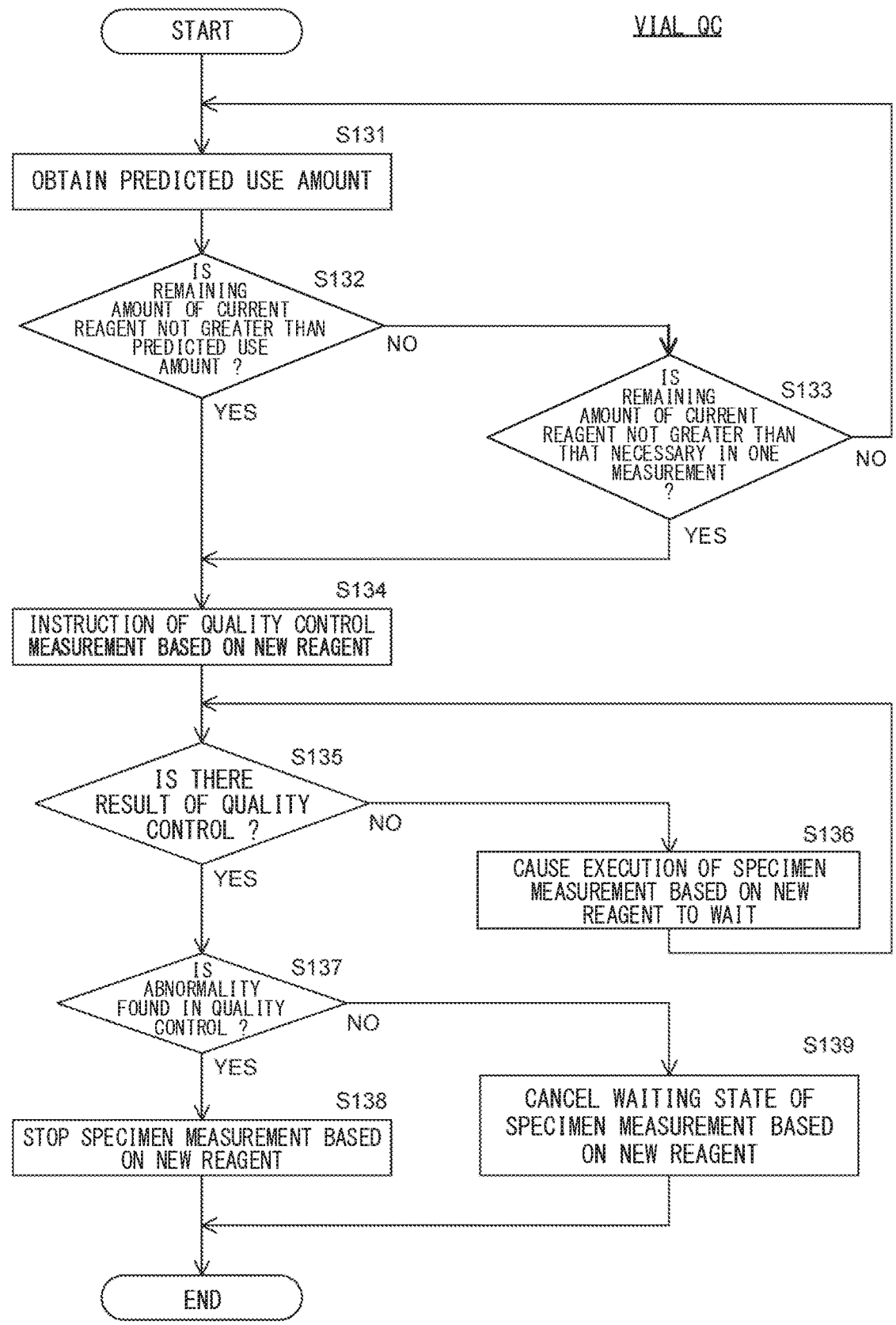
FIG. 19 is a flow chart showing a process of the vial QC according to Embodiment 1.

As shown in FIG. 19, in step S131, the controller 331 obtains a predicted use amount of the reagent that will be necessary in the time period Tc required for one quality control measurement. Specifically, as described with reference to FIGS. 9B and 9C, with respect to the measurement item, the controller 331 calculates, on the basis of the history information stored in the storage unit 332, an average Na of the number of times of specimen measurement on a day of week and in a time frame to which the current time belongs. On the basis of multiplication of the time period Tc and the average number of times Na, the controller 331 obtains an estimated number of times Nc of specimen measurement executable in the time period Tc required for one quality control measurement. Then, the controller 331 multiplies the reagent amount necessary for one specimen measurement with the estimated number of times Nc, to obtain a predicted use amount of the reagent.

Subsequently, in step S132, the controller 331 determines whether or not the remaining amount of the current reagent is not greater than the predicted use amount obtained in step S131. As described above, the remaining amount of the current reagent is stored in the storage unit 332 and is updated every dispensing of the reagent. When the remaining amount of the current reagent is not greater than the predicted use amount, the controller 331 transmits, in step S134, an instruction to perform a quality control measurement based on a new reagent, to the controller 321 of the measurement section 32, thereby causing the measurement section 32 to perform a quality control measurement. In this case, in step S62 in FIG. 17B, the controller 321 of the measurement section 32 causes a quality control measurement not based on the current reagent but based on the new reagent to be performed.

When the remaining amount of the current reagent is greater than the predicted use amount, the controller 331 determines, in step S133, whether or not the remaining amount of the current reagent is not greater than a reagent amount to be used in one specimen measurement. When the remaining amount of the current reagent is not greater than the reagent amount to be used in one specimen measurement, i.e., when due to the shortage of the remaining current reagent, the specimen measurement cannot be performed with use of the current reagent, the controller 331 advances the process to step S134, and causes a quality control measurement based on a new reagent to be performed. Meanwhile, when the remaining amount of the current reagent is greater than the reagent amount to be used in one specimen measurement, there is no need to immediately start a quality control measurement based on a new reagent. Thus, the controller 331 returns the process to step S131.

Subsequently, in step S135, the controller 331 determines whether or not a result of the quality control measurement based on the new reagent performed in step S134 has been obtained. When the result of the quality control measurement based on the new reagent has not been obtained, the controller 331 causes, in step S136, execution of the specimen measurement based on the new reagent to wait. That is, when the result of the quality control regarding the new reagent has not been obtained, whether or not the new reagent is in an appropriate state cannot be determined. Therefore, the controller 331 transmits, to the controller 321 of the measurement section 32, an instruction of causing execution of a specimen measurement using the new reagent to wait so that the specimen measurement using the new reagent is not started until a result of the quality control measurement based on the new reagent is obtained. Accordingly, in step S42 in FIG. 16B, the controller 321 causes the specimen measurement using the new reagent for the target measurement item to wait.

Upon obtaining the result of the quality control measurement based on the new reagent, the controller 331 performs, in step S137, analysis regarding the quality control based on the result of the quality control measurement, and determines whether or not there is an abnormality in the new reagent. When having determined that there is an abnormality in the new reagent, the controller 331 stops, in step S138, the specimen measurement based on the new reagent. Accordingly, the specimen measurement based on the new reagent is not started, and the specimen measurement for the measurement item is stopped at the time point when there is no remaining current reagent. Meanwhile, when having determined that there is no abnormality in the new reagent, the controller 331 transmits, in step S139, an instruction to cancel the waiting state of the specimen measurement using the new reagent, to the controller 321 of the measurement section 32 so that the waiting state of the specimen measurement using the new reagent is canceled. Accordingly, when the controller 321 has received an instruction of a specimen measurement for the target measurement item, the controller 321 causes the specimen measurement using the new reagent to be performed in step S42 in FIG. 16B. Then, the process in FIG. 19 ends.

According to the process in FIG. 19, a quality control measurement based on a new reagent is performed in accordance with a predicted use amount. Therefore, normally, a waiting time for a specimen measurement using a new reagent as shown in FIG. 8B is not caused. However, depending on the frequency at which specimen measurements are actually performed, a waiting time for a specimen measurement using a new reagent could be caused as shown in FIG. 8B. Also in such a case, according to Embodiment 1, when it has been determined that there is no abnormality in the new reagent, the waiting state is quickly canceled in step S139. Thus, the specimen measurement using the new reagent can be quickly started.

Embodiment 2

In Embodiment 2, for each measurement item, recommendation information that suggests which quality control in the quality control group is preferable is displayed on the reception screen 410. In Embodiment 2, only the configurations and processes in FIGS. 20 to 23 described below are different, when compared with Embodiment 1. The other configurations in Embodiment 2 are the same as those in Embodiment 1.

As shown in FIG. 20, when compared with the reception screen 410 of Embodiment 1 shown in FIG. 12, the reception screen 410 of Embodiment 2 further includes a reagent property display region 431, a reagent stability display region 432, and comment regions 433, 434. The display contents in the reagent property display region 431, the reagent stability display region 432, and the comment regions 433, 434 are recommendation information that suggests a preferable quality control.

In the reagent property display region 431, the property of the reagent (hereinafter, "reagent property") is displayed. In Embodiment 2, the reagent property denotes a freeze-dried article or a liquid-state article. In the reagent stability display region 432, the stability of the reagent (hereinafter, "reagent stability") is displayed. In Embodiment 2, the reagent stability is information indicating how long the good quality state of the reagent is maintained, and is expressed by a time period such as 5 hours or 10 hours, for example. The reagent stability may be expressed as "good" or "bad".

The storage unit 332 of the analysis section 33 stores pieces of reagent information of respective reagents contained in all the reagent containers 21 set on the reagent table 260. The reagent information includes information that indicates which of a freeze-dried article and a liquid-state article the reagent is, and information that indicates the reagent stability. When causing the display unit 333 to display the reception screen 410, the controller 331 reads out reagent information to be used for the measurement item, from the storage unit 332. Then, on the basis of the read out reagent information, the controller 331 causes the reagent property to be displayed in the reagent property display region 431, and causes the reagent stability to be displayed in the reagent stability display region 432.

A guide for determining which quality control in the quality control group is preferable is displayed in the comment region 433. Quality controls that are preferably set in actuality are specifically displayed in the comment region 434.

Here, which quality control in the quality control group is preferably set in which case is determined in advance as shown in FIGS. 21A and 21B.

As shown in FIG. 21A, on the basis of the test number and the reagent stability for a target measurement item, a preferable quality control is determined from among the time QC, the time interval QC, and the test number QC. In FIG. 21A, the test number denotes the frequency of specimen measurements to be performed for the target measurement item. In a case where the reagent stability is good, the time QC is preferable irrespective of the test number. In a case where the reagent stability is bad, the test number QC is preferable when the test number is large, and the time interval QC is preferable when the test number is small. As shown in FIG. 21B, whether the vial QC is preferably set is determined on the basis of the reagent property for the target measurement item. In a case where the reagent property corresponds to a freeze-dried article, the vial QC is preferably set.

With reference back to FIG. 20, the contents shown in the tables in FIGS. 21A, 21B are displayed as messages in the comment region 433. On the basis of the history information as shown in FIG. 9B, the controller 331 determines whether or not the test number for the measurement item is large, i.e., whether or not specimen measurements for the measurement item have been performed at a high frequency. In addition, the controller 331 reads out, from the storage unit 332, the reagent stability to be used for the measurement item, and determines the read out reagent stability. On the basis of the determination result and the rules shown in FIGS. 21A, 21B, the controller 331 determines a preferable quality control. Then, the controller 331 causes the determined quality control to be displayed in the comment region 434.

As described above, if the recommendation information that suggests a preferable quality control is displayed in the reagent property display region 431, the reagent stability display region 432, and the comment regions 433, 434, the operator can visually understand which quality control in the quality control group is preferably performed, by referring to the recommendation information. With reference to the reagent property displayed in the reagent property display region 431, the reagent stability displayed in the reagent stability display region 432, and the comment displayed in the comment region 434, a preferable quality control can be determined. Thus, the display of these pieces of information as recommendation information enables the operator to determine a preferable quality control in the quality control group.

Not limited to a preferable quality control being displayed in the comment region 434, a marker such as an icon or a message may be displayed in the vicinity of an operation portion for setting a quality control determined as preferable. For example, when the vial QC is preferable, a marker may be displayed in the vicinity of the check box 414 in FIG. 20. When the time QC is preferable, a marker may be displayed in the vicinity of the check box 421 in FIG. 13. When the time interval QC is preferable, a marker may be displayed in the vicinity of the radio button 424a in FIG. 13. When the test number QC is preferable, a marker may be displayed in the vicinity of the radio button 425a in FIG. 13.

Figure 22:
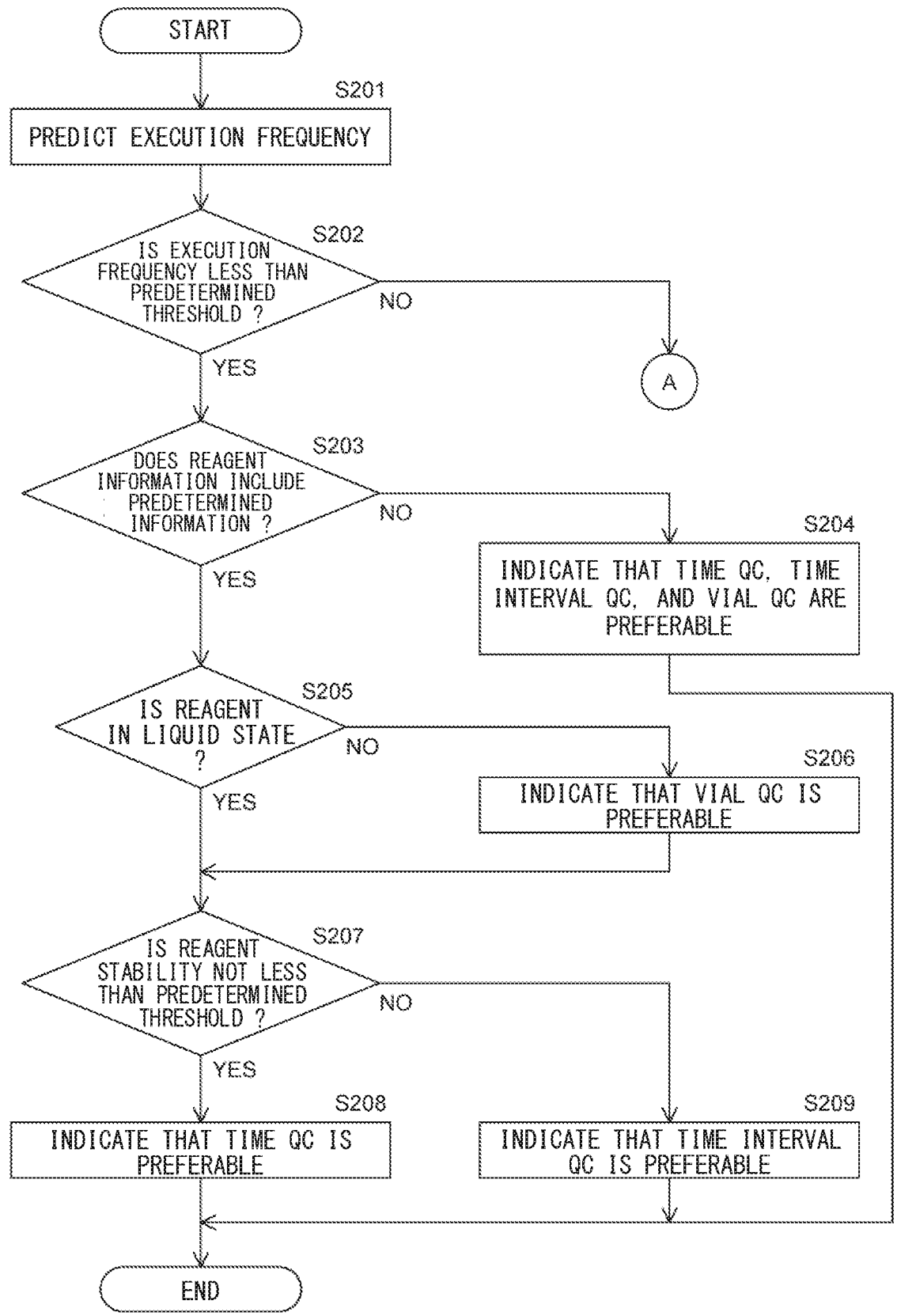
FIG. 22 is a flow chart showing a display process of recommendation information in a comment region according to Embodiment 2.
Figure 23:
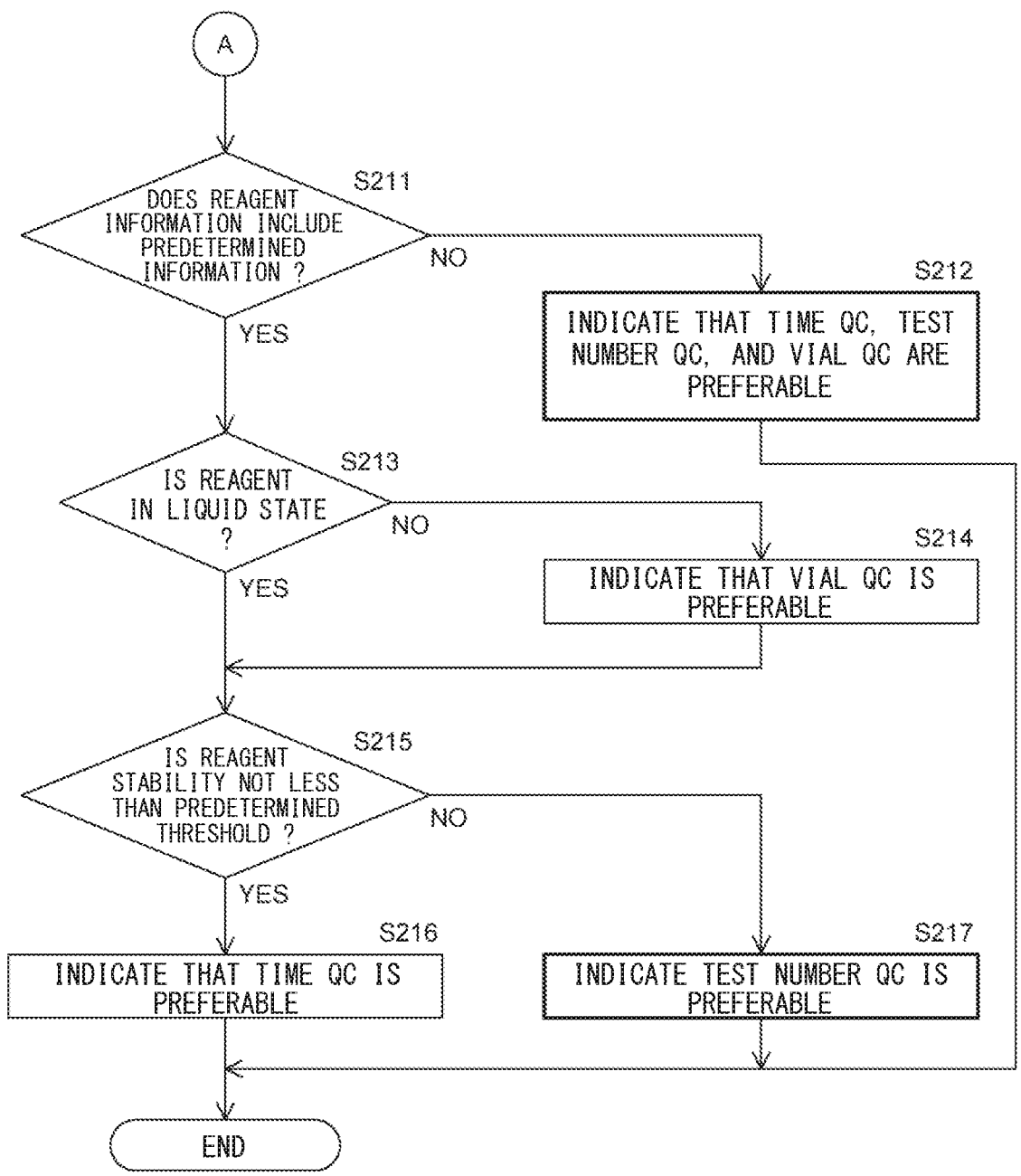
FIG. 23 is a flow chart showing a display process of recommendation information in a comment region according to Embodiment 2.

With reference to FIGS. 22, 23, a display process of recommendation information in the comment region 434 is described. When the operator operates the input unit 334 to select a measurement item on the edit measurement item selection screen 402, and operates the item edit button 402b, the controller 331 starts a process shown in FIGS. 22, 23.

As shown in FIG. 22, in step S201, the controller 331 predicts an execution frequency of specimen measurement for the measurement item. Specifically, on the basis of history information, the controller 331 obtains, as a predicted value of the execution frequency, the number of times of specimen measurement for the measurement item per predetermined time period in a predetermined period. The predetermined period in this case is 50 weeks, for example, and the predetermined time period is 1 hour, for example. The controller 331 may obtain, as a predicted value of the execution frequency, the number of times of specimen measurement for the measurement item in a predetermined period.

In step S202, the controller 331 determines whether or not the execution frequency obtained in step S201 is less than a predetermined threshold. The predetermined threshold used in step S202 is an execution frequency threshold that allows determination as to whether or not the frequency of the specimen measurement is high, and that allows determination as to which of the time interval QC and the test number QC is preferable.

Thus, when the execution frequency is predicted on the basis of the history information, it is possible to appropriately determine which of the time interval QC and the test number QC is preferable, in accordance with the magnitude of the execution frequency, as described later. Therefore, a preferable quality control can be appropriately displayed as the recommendation information.

When the execution frequency is less than the predetermined threshold, the controller 331 determines, in step S203, whether or not the reagent information of the reagent to be used for the measurement item includes predetermined information. As described above, the reagent information is stored in the storage unit 332, and normally includes reagent property and reagent stability. In step S203, the controller 331 reads out the reagent information from the storage unit 332 and determines whether or not the read out reagent information includes reagent property and reagent stability.

When the reagent information does not include the reagent property and the reagent stability, the controller 331 causes, in step S204, an indication that the time QC, the time interval QC, and the vial QC are preferable, to be displayed in the comment region 434 of the reception screen 410. When the reagent information includes the reagent property and the reagent stability, the controller 331 advances the process to step S205.

In step S205, on the basis of the reagent property included in the reagent information, the controller 331 determines whether or not the reagent for the measurement item is a liquid-state article. When the reagent is a freeze-dried article, the controller 331 causes, in step S206, an indication that the vial QC is preferable, to be displayed in the comment region 434 of the reception screen 410. When the reagent is a liquid-state article, the controller 331 advances the process to step S207.

In step S207, on the basis of the reagent stability included in the reagent information, the controller 331 determines whether or not the reagent stability for the measurement item is not less than a predetermined threshold. The predetermined threshold used in step S207 is a threshold that allows determination as to whether the reagent stability is high or low, and is a threshold that allows determination as to which of the time QC and the time interval QC is preferable. In a case where the reagent stability is defined as a time period for which the quality of the reagent is maintained in a good state, the predetermined threshold used in step S207 is set to a time period of 5 hours or the like, for example.

When the reagent stability is not less than the predetermined threshold, the controller 331 causes, in step S208, an indication that the time QC is preferable, to be displayed in the comment region 434 of the reception screen 410. Meanwhile, when the reagent stability is less than the predetermined threshold, the controller 331 causes, in step S209, an indication that the time interval QC is preferable, to be displayed in the comment region 434 of the reception screen 410.

When it has been determined that the execution frequency is not less than the predetermined threshold in step S202, the controller 331 advances the process to step S211 in FIG. 23.

In steps S211 to S217 shown in FIG. 23, when compared with steps S203 to S209 in FIG. 22, steps S204 and S209 are replaced by steps S212 and S217, respectively. Steps S211 and S213 to S216 are the same as steps S203 and S205 to S208. In the following, steps S212 and S217 are described.

When it has been determined that the reagent information does not include the reagent property and the reagent stability in step S211, the controller 331 causes, in step S212, an indication that the time QC, the test number QC, and the vial QC are preferable to be displayed in the comment region 434 of the reception screen 410. In step S215, when it has been determined that the reagent stability is less than a predetermined threshold, the controller 331 causes, in step S217, an indication that the test number QC is preferable, to be displayed in the comment region 434 of the reception screen 410.

When it has been determined that the reagent stability is not less than the predetermined threshold in step S207, S215, an indication that the time QC is preferable is displayed in the comment region 434 of the reception screen 410. Accordingly, when the reagent stability is high, the operator can visually understand that the time QC is preferable. When it has been determined that the reagent property corresponds to a freeze-dried article in step S205, S213, an indication that the vial QC is preferable is displayed in the comment region 434 of the reception screen 410. Accordingly, when the reagent is a freeze-dried article, the operator can visually understand that the vial QC is preferable.

Embodiment 3

In Embodiment 3, for each measurement item, a candidate quality control to be performed is selected from among the quality controls included in the quality control group. In Embodiment 3, when compared with Embodiment 1, only the process shown in FIGS. 24, 25 described below is different. The other configurations in Embodiment 3 are the same as those in Embodiment 1.

Figure 24:
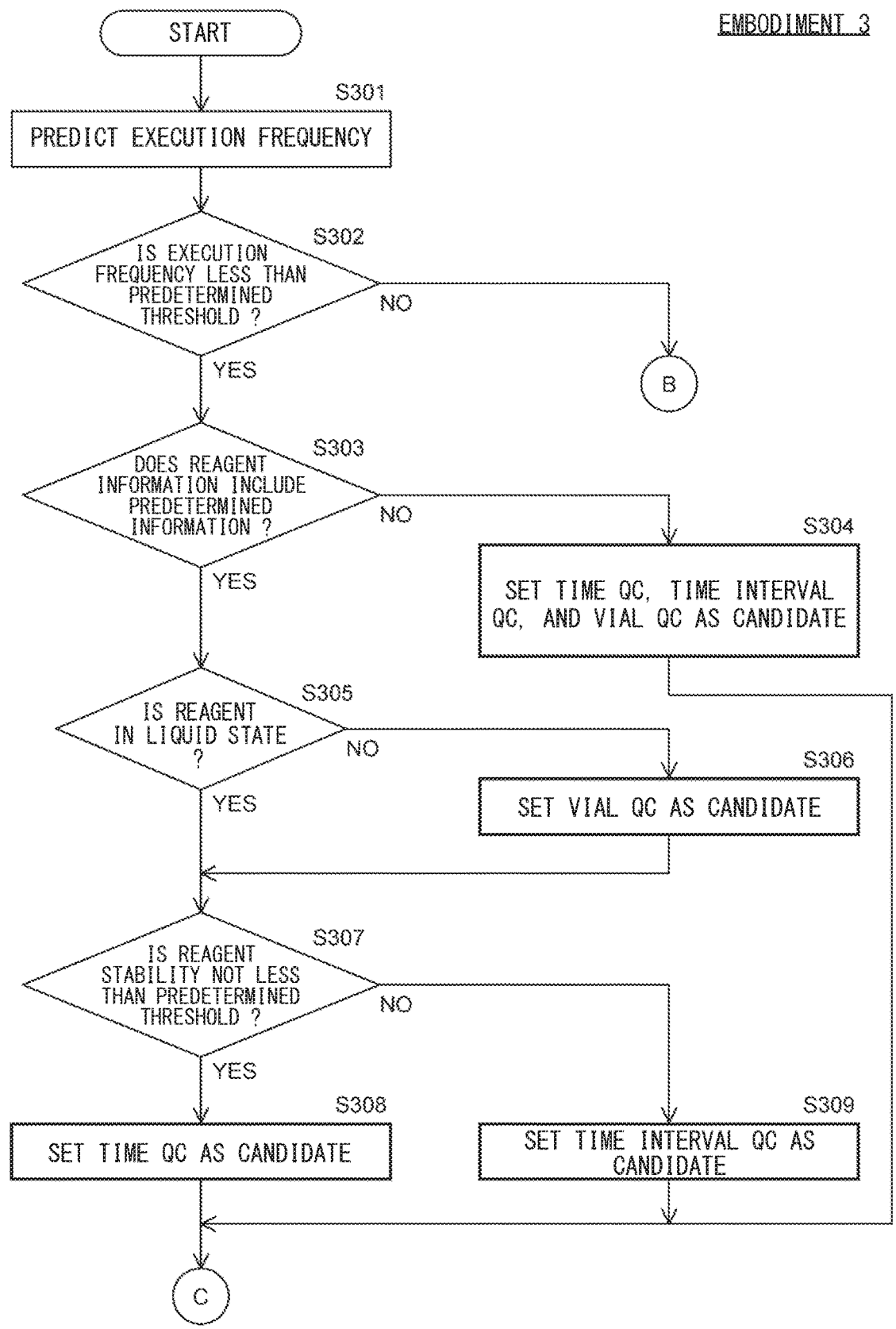
FIG. 24 is a flow chart showing a process of selecting a candidate quality control to be performed according to Embodiment 3.
Figure 25:
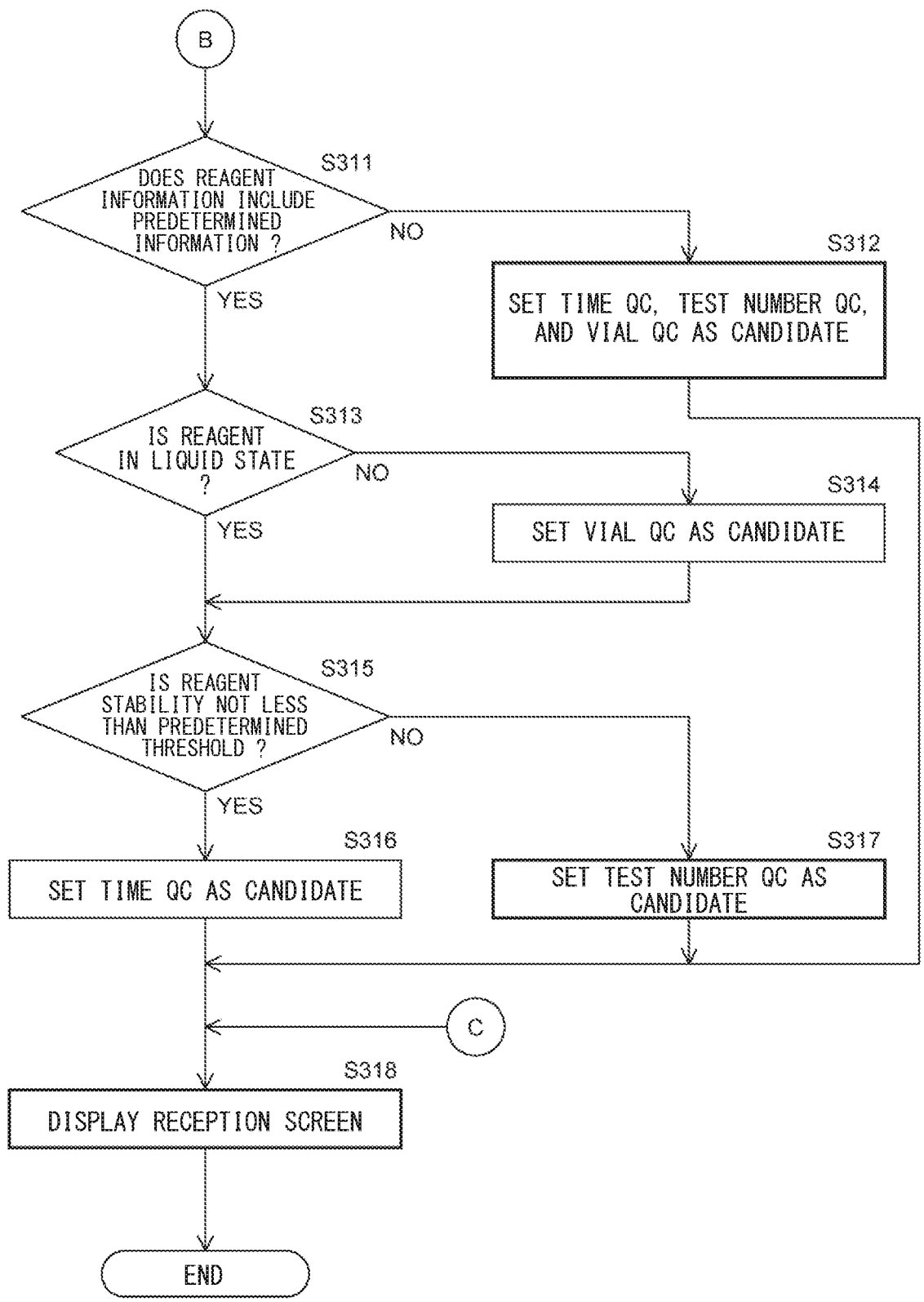
FIG. 25 is a flow chart showing a process of selecting a candidate quality control to be performed according to Embodiment 3.

With reference to FIGS. 24, 25, a process of selecting a candidate quality control to be performed is described. When a reagent container 21 has been set in the reagent table 260 and the set reagent container 21 has been registered through a screen for registering a reagent, the controller 331 starts the process shown in FIGS. 24, 25 with respect to a measurement item for which the reagent contained in this reagent container 21 is to be used. The start timing of the process in FIGS. 24, 25 is not limited to the timing at which the reagent container 21 is registered. For example, the controller 331 may start the process in FIGS. 24, 25 for each measurement item at a predetermined time interval.

The processes of steps S301 to S303, S305, and S307 in FIG. 24 are the same as the processes of steps S201 to S203, S205, and S207 in FIG. 22. Therefore, for convenience, in the description with respect to FIG. 24 below, the processes of steps S304, S306, S308, and S309 are described.

When it has been determined that the reagent information does not include the reagent property and the reagent stability in step S303, the controller 331 sets, in step S304, the time QC, the time interval QC, and the vial QC as candidate quality controls to be performed. When it has been determined that the reagent is a freeze-dried article in step S305, the controller 331 sets, in step S306, the vial QC as a candidate quality control to be performed. In step S307, when it has been determined that the reagent stability is not less than a predetermined threshold, the controller 331 sets, in step S308, the time QC as a candidate quality control to be performed. When it has been determined that the reagent stability is less than the predetermined threshold in step S307, the controller 331 sets, in step S309, the time interval QC as a candidate quality control to be performed. When step S308, S309 ends, the controller 331 advances the process to step S318 in FIG. 25.

When it has been determined that the execution frequency is not less than a predetermined threshold in step S302, the controller 331 advances the process to step S311 in FIG. 25.

The processes of steps S311 and S313 to S316 in FIG. 25 are the same as the processes of steps S303 and S305 to S308 in FIG. 24. Thus, for convenience, in the description regarding FIG. 25 below, the processes of steps S312, S317, and S318 are described.

When it has been determined that the reagent information does not include the reagent property and the reagent stability in step S311, the controller 331 sets, in step S312, the time QC, the test number QC, and the vial QC as candidate quality controls to be performed. When it has been determined that the reagent stability is less than a predetermined threshold in step S315, the controller 331 sets, in step S317, the test number QC as a candidate quality control to be performed.

In step S318, the controller 331 causes the display unit 333 to display the reception screen 410, 420 in a state where execution of each candidate quality control to be performed that has been set in the processes of the previous steps, i.e., steps S301 to S309 and S311 to S317, is set.

Specifically, when having set the vial QC as a candidate quality control to be performed, the controller 331 causes the reception screen 410 to be displayed in a state where the check box 414 in FIG. 12 is checked. When having set the time QC, the time interval QC, and the test number QC as candidate quality controls to be performed, the controller 331 causes the reception screen 410 to be displayed in a state where the check box 412 in FIG. 12 is checked. When having set the time QC as a candidate quality control to be performed, the controller 331 causes the reception screen 420 to be displayed in a state where the check box 421 in FIG. 13 is checked. When having set the time interval QC or the test number QC as a candidate quality control to be performed, the controller 331 causes the reception screen 420 to be displayed in a state where the check box 423 in FIG. 13 is checked. When having set the time interval QC as a candidate quality control to be performed, the controller 331 causes the reception screen 420 to be displayed in a state where the radio button 424a in FIG. 13 is selected. When having set the test number QC as a candidate quality control to be performed, the controller 331 causes the reception screen 420 to be displayed in a state where the radio button 425a in FIG. 13 is selected.

In step S318, after the reception screen 410, 420 is displayed in a state where the candidate quality controls to be performed are set, the operator confirms the quality controls set as the candidate quality controls to be performed. Then, the operator operates relevant portions of the reception screen 410, 420 to correct the candidate quality controls to be performed or a set value and the like of each quality control as necessary. Then, the operator operates the registration button 415 of the reception screen 410 to fix the quality controls to be performed.

As described above, according to Embodiment 3, when a candidate quality control to be performed is selected, the operator can save the trouble of determining which quality control should be performed. In addition, when an execution frequency is predicted on the basis of the history information in step S301, either the time interval QC or the test number QC is selected at least as a candidate quality control to be performed, in accordance with the magnitude of the execution frequency. Thus, the operator can save the trouble of selecting a quality control after taking the execution frequency into consideration.

In a case where it has been determined that the reagent stability is not less than the predetermined threshold in step S307, S315, the time QC is selected as a candidate quality control to be performed. Accordingly, the operator can save the trouble of selecting the time QC after determining that the reagent stability is high. In a case where it has been determined that the reagent property corresponds to a freeze-dried article in step S305, S313, the vial QC is selected as a candidate quality control to be performed. Accordingly, the operator can save the trouble of selecting the vial QC after determining that the reagent is a freeze-dried article.

After the processes of steps S301 to S309 in FIG. 24, and steps S311 to S317 in FIG. 25, the controller 331 causes, in step S318, the display unit 333 to display the reception screen 410, 420 for receiving settings of the quality control to be performed on the basis of the selected candidate quality control to be performed. Accordingly, with respect to the quality control selected by the controller 331 as the candidate quality control to be performed, the operator can smoothly input settings such as whether or not to perform the quality control, specific parameters, etc.

In step S318 shown in FIG. 25, the controller 331 may set the selected candidate quality control to be performed, as the quality control to be performed, without causing the reception screen 410, 420 to be displayed. Accordingly, the candidate quality control to be performed can be executed, while the operator is not required to confirm the candidate quality control to be performed, or is not required to input settings such as whether or not to perform the quality control, specific parameters, etc. If the quality control to be performed is automatically set in this manner, the operator can save the trouble of setting the quality control to be performed, on the basis of the candidate quality control to be performed.

What is claimed is:

1. A specimen analyzer configured to perform analysis on a specimen for a plurality of measurement items, the specimen analyzer comprising:
a measurement section comprising a detector, the measurement section configured to perform a specimen measurement for measuring a measurement sample, the measurement sample prepared from a specimen and a reagent corresponding to a measurement item, the measurement item from among the plurality of measurement items, and the measurement section further configured to perform a quality control measurement for measuring another measurement sample prepared from a quality control substance and the reagent corresponding to the measurement item; and
a controller programmed to set a quality control for each of the measurement items, the quality control being from a quality control group that includes at least two types of quality controls selected from:
a first quality control in which the quality control measurement is performed at a predetermined time,
a second quality control in which the quality control measurement is performed every time the specimen measurement is performed a predetermined number of times, and
a third quality control in which the quality control measurement is performed every predetermined time interval,
the controller being programmed to receive a selection of the measurement item and control the measurement section to measure the another measurement sample in accordance with the quality control set by the controller for the received measurement item.

2. The specimen analyzer of claim 1, wherein
the measurement section includes a reagent dispensing unit configured to open a cap portion covering an opening of a reagent container and dispense the reagent contained in the reagent container when the measurement sample is prepared.

3. The specimen analyzer of claim 1, wherein
the measurement section includes:
a light source part configured to apply light to the measurement sample; and
a light receiver configured to receive light that has been generated from the measurement sample, and
the specimen measurement and the quality control measurement are each a measurement related to blood coagulation.

4. The specimen analyzer of claim 1, wherein
the controller is programmed to alternatively set either one of the second quality control and the third quality control for the respective measurement items.

5. The specimen analyzer of claim 1, wherein
when the first quality control and the second quality control are set for the received measurement item, the controller is programmed to reset a count of a number of times the specimen is measured according to the second quality control when the quality control measurement is performed based on the first quality control, and/or
when the first quality control and the third quality control are set for the received measurement item, the controller is programmed to reset a count of an elapsed time in the third quality control when the quality control measurement is performed based on the first quality control.

6. The specimen analyzer of claim 1, wherein
the quality control group further includes a fourth quality control in which, when a remaining amount of the reagent in a first reagent container has become smaller than a predetermined amount, the quality control measurement is performed based on a reagent in a second reagent container of a same reagent type corresponding to the received measurement item.

7. The specimen analyzer of claim 6, wherein
the controller is programmed to estimate a number of times the specimen measurement is executable in a time period required for the quality control measurement, and is programmed to calculate, as the predetermined amount, a reagent amount necessary for the specimen measurement to be performed the estimated number of times.

8. The specimen analyzer of claim 7, comprising
a memory configured to store history information regarding past execution history of the specimen measurement performed by the measurement section, wherein
the controller is programmed to estimate the number of times based on the history information.

9. The specimen analyzer of claim 8, wherein
the number of times is a number of times of the specimen measurement predicted to be performed in a day of a week or a predetermined time frame to which a current time belongs.

10. The specimen analyzer of claim 1, comprising
a display, wherein
the controller is programmed to cause the display to display a reception screen for receiving a setting of each quality control included in the quality control group, and the controller is programmed to cause the display to display, for each measurement item, recommendation information that suggests which of the quality controls in the quality control group is preferable.

11. The specimen analyzer of claim 10, comprising
a memory configured to store history information regarding past execution history of the specimen measurement performed by the measurement section, wherein
the controller is programmed to cause the display unit to display the recommendation information based on the history information.

12. The specimen analyzer of claim 11, wherein
the controller is programmed to:
predict an execution frequency of the specimen measurement based on the history information;
cause, when the execution frequency is greater than an execution frequency threshold, the recommendation information to include an indication that the second quality control is preferable; and
cause, when the execution frequency is smaller than the execution frequency threshold, the recommendation information to include an indication that the third quality control is preferable.

13. The specimen analyzer of claim 10, wherein
the controller is programmed to cause the display unit to display the recommendation information based on reagent information of the reagent.

14. The specimen analyzer of claim 13, wherein
the controller is programmed to cause, when a value indicating reagent stability is greater than a reagent stability threshold, the recommendation information to include an indication that the first quality control is preferable.

15. The specimen analyzer of claim 13, wherein
the quality control group further includes a fourth quality control in which, when a remaining amount of a reagent in a first reagent container has become smaller than a predetermined amount, the quality control measurement is performed on the basis of a reagent in a second reagent container containing a reagent of the same reagent type corresponding to the received measurement item, and
the controller is programmed to cause, when a reagent property corresponds to a freeze-dried article, the recommendation information to include an indication that the fourth quality control is preferable.

16. The specimen analyzer of claim 1, wherein
the controller is programmed to select, for each measurement item, a candidate quality control to be performed from among the quality controls included in the quality control group.

17. The specimen analyzer of claim 16, further comprising
a memory configured to store history information regarding past execution history of the specimen measurement performed by the measurement section, wherein
the controller is programmed to predict an execution frequency of the specimen measurement for each measurement item based on the history information, and is programmed to select the candidate quality control to be performed based on the predicted execution frequency.

18. The specimen analyzer of claim 17, wherein
the controller is programmed to:
select, when the execution frequency is greater than an execution frequency threshold, at least the second quality control as a candidate quality control to be performed; and
select, when the execution frequency is smaller than the execution frequency threshold, at least the third quality control as a candidate quality control to be performed.

19. A specimen analysis method for performing analysis on a specimen for a plurality of measurement items, the specimen analysis method comprising:
setting a quality control for each of the measurement items, each of the measurement items corresponding to a respective specimen and a respective reagent, and the quality control being set for each of the respective measurement items from a quality control group that includes at least two types of quality controls selected from:
a first quality control in which the quality control measurement is performed at a predetermined time,
a second quality control in which the quality control measurement is performed every time the specimen measurement is performed a predetermined number of times, and
a third quality control in which the quality control measurement is performed every predetermined time interval;
receiving a measurement item from among the plurality of measurement items;
selectively performing, in accordance with the received measurement item, a specimen measurement to measure a measurement sample prepared from the respective specimen and the respective reagent corresponding to the received measurement item; and
selectively performing, in accordance with the quality control set for the received measurement item, a quality control measurement for measuring another measurement sample prepared from a quality control substance and the reagent corresponding to the received measurement item.

* * * * *

UNITED STATES PATENT AND TRADEMARK OFFICE
CERTIFICATE OF CORRECTION

PATENT NO. : 11,604,201 B2
APPLICATION NO. : 16/697423
DATED : March 14, 2023
INVENTOR(S) : Hiroshi Kurono It is certified that error appears in the above-identified patent and that said Letters Patent is hereby corrected as shown below:

In the Claims

In Column 37, Line 26, delete "unit"

Signed and Sealed this
Twenty-fifth Day of April, 2023

*Katherine Kelly Vidal*

Katherine Kelly Vidal
*Director of the United States Patent and Trademark Office*